United States Patent
Egan et al.

(10) Patent No.: US 9,222,875 B2
(45) Date of Patent: *Dec. 29, 2015

(54) HAND-HELD SCANNER SYSTEMS AND METHODS FOR READING POINT OF CARE TEST RESULTS

(71) Applicant: NEXUS DX, INC., San Diego, CA (US)

(72) Inventors: Richard Egan, Oceanside, CA (US); Graham Lidgard, La Jolla, CA (US); David Booker, Oceanside, CA (US)

(73) Assignee: Nexus Dx, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/133,199

(22) Filed: Dec. 18, 2013

(65) Prior Publication Data

US 2014/0343860 A1    Nov. 20, 2014

Related U.S. Application Data

(62) Division of application No. 12/756,157, filed on Apr. 7, 2010, now Pat. No. 8,638,441.

(60) Provisional application No. 61/167,485, filed on Apr. 7, 2009.

(51) Int. Cl.
  *G01N 21/01*  (2006.01)
  *G01N 21/55*  (2014.01)
  *G01N 21/84*  (2006.01)
  *G01N 33/487*  (2006.01)
  *G06F 19/00*  (2011.01)

(52) U.S. Cl.
  CPC ............... *G01N 21/01* (2013.01); *G01N 21/84* (2013.01); *G01N 21/8483* (2013.01); *G01N 33/487* (2013.01); *G01N 2201/0446* (2013.01); *G01N 2201/126* (2013.01); *G06F 19/366* (2013.01)

(58) Field of Classification Search
  USPC ............. 356/445, 244, 246, 72–73; 435/7.25, 435/7.94, 287.2; 436/514, 518, 169, 172, 436/175
  See application file for complete search history.

(56) References Cited

U.S. PATENT DOCUMENTS

| 5,408,535 A | 4/1995 | Howard et al. |
| 6,551,842 B1 | 4/2003 | Carpenter |

(Continued)

FOREIGN PATENT DOCUMENTS

| JP | 2002-206088 A | 7/2002 |
| JP | 2004-504607 T | 2/2004 |

(Continued)

OTHER PUBLICATIONS

PCT Application PCT/SD2010/30309 International Search Report mailed Nov. 17, 2010.

(Continued)

*Primary Examiner* — Sang Nguyen

(74) *Attorney, Agent, or Firm* — Knobbe, Martens, Olson & Bear, LLP

(57) ABSTRACT

A diagnostic assay system including a test device and a scanning device are described. In one implementation, the scanning device includes a source of electromagnetic radiation, an optics assembly, a detector, and a microprocessor disposed within a chassis. The test device and scanning device may be configured to be movable relative to each other during operation of the scanning device.

20 Claims, 12 Drawing Sheets

(56) References Cited

U.S. PATENT DOCUMENTS

| | | |
|---|---|---|
| 6,614,525 B1 | 9/2003 | Engelhardt et al. |
| 6,867,051 B1 * | 3/2005 | Anderson et al. ............. 436/518 |
| 6,936,476 B1 | 8/2005 | Anderson et al. |
| 7,335,898 B2 | 2/2008 | Donders et al. |
| 7,344,081 B2 | 3/2008 | Tseng |
| 7,365,849 B2 * | 4/2008 | Yao et al. ...................... 356/402 |
| 7,444,005 B2 | 10/2008 | Bachur, Jr. et al. |
| 7,521,260 B2 * | 4/2009 | Petruno et al. ................ 436/514 |
| 7,768,638 B2 | 8/2010 | Feng |
| 7,932,099 B2 | 4/2011 | Egan et al. |
| 8,021,648 B2 | 9/2011 | Rodriguez-Kabana |
| 8,183,059 B2 | 5/2012 | Siciliano et al. |
| 8,722,424 B2 * | 5/2014 | Miyoshi et al. ............... 436/514 |
| 8,789,756 B2 * | 7/2014 | Austera et al. ........... 235/462.05 |
| 2002/0117632 A1 | 8/2002 | Hakamata et al. |
| 2002/0151043 A1 | 10/2002 | Gordon |
| 2006/0052709 A1 | 3/2006 | DeBaryshe et al. |
| 2006/0292040 A1 | 12/2006 | Wickstead et al. |
| 2010/0255510 A1 | 10/2010 | Wang et al. |

FOREIGN PATENT DOCUMENTS

| | | |
|---|---|---|
| JP | 2004-170217 A | 6/2004 |
| JP | 2008-542708 T | 11/2008 |
| WO | WO 2007/098184 | 12/2008 |
| WO | WO 2009/014787 | 8/2009 |

OTHER PUBLICATIONS

Office Action dated Nov. 6, 2014 in related Japanese Application No. 2012-504841.

* cited by examiner

HAND-HELD SCANNER SYSTEMS AND METHODS FOR READING POINT OF CARE TEST RESULTS

CROSS-REFERENCE TO RELATED APPLICATIONS

The present application is a continuation of U.S. Utility application Ser. No.: 12/756,157, filed on Apr. 7, 2010, now issued as U.S. Pat. No. 8,638,441, which claims priority under 35 U.S.C. §119(e) to U.S. Provisional Patent Application Ser. No. 611167,485, entitled HAND-HELD SCANNER FOR READING POINT OF CARE TEST RESULTS, filed on Apr. 7, 2009, the contents of which are incorporated by reference herein in their entirety for all purposes.

FIELD OF THE INVENTION

This application is directed generally to systems, devices and methods for providing point-of-care testing. More particularly, but not exclusively, the present invention is directed to handheld test systems and associated methods, including scanners and associated test devices. The test systems may be configured to provide portable, disposable point-of-care tests, as well as associated test processing, analysis and test results and data.

BACKGROUND

Point-of-care test device readers and/or drive units are known in the art, such as those used for diagnostics of infectious diseases. Currently available readers are expensive and large (e.g., typically about the size of an antique desk phone or similar device). In addition, they generally consume substantial amounts of power and are not easily portable. For example, currently known readers are not readily capable of being placed in a user's pocket and/or taken from patient to patient at the bedside or point-of-care, making them cumbersome and expensive to use.

Accordingly, there is a need in the art for improved point-of-care testing systems, devices and methods.

SUMMARY

The present invention is directed generally to devices and methods for providing point-of-care test device readers.

In one aspect, a diagnostic assay system is disclosed, comprising: a test device including a test strip having one or more test lines and one or more indicia; and a scanning device comprising: a source of electromagnetic radiation; an optics assembly disposed to direct the electromagnetic radiation; a detector disposed to receive an emission or reflection from the test strip; a microprocessor; and a chassis; wherein the test device and scanning device are configured to be movable relative to each other during operation of the scanning device and wherein the microprocessor is configured to generate test result data based at least in part on the indicia and one or more of the test lines.

In another aspect, a method of assaying a sample to detect an analyte of interest is disclosed, the method comprising the steps of: providing a sample from a sample collection device to a test device, wherein the test device comprises one or more test lines having immobilized thereto a capture moiety specifically binding directly or indirectly one or more analytes of interest, and wherein the indicia are positioned on a surface of the test device adjacent the one or more test lines; moving the test device relative to a scanning device so as to read one or more of the test lines and one or more of the indicia; generating test result data based at least in part on the read of one or more of the indicia and the one or more test lines; and storing the test result data in a memory.

In another aspect, a test device is disclosed, comprising a substrate including: a test strip having one or more test lines; and one or more indicia; wherein the indicia are disposed on the substrate so at to facilitate registration of the test device with respect to a scanner so as to compensate for presentation of the test device to the scanner.

In another aspect, a scanner is disclosed, comprising: a source of electromagnetic radiation; an optics assembly disposed to direct the electromagnetic radiation; a detector disposed to receive an emission or reflection from a test device; a microprocessor; and a chassis; wherein the microprocessor is configured to generate test result data based on one or more indicia associated disposed on the test device and one or more test lines disposed on the test device.

In another aspect, a diagnostic assay system is disclosed. In various embodiments, the diagnostic assay system includes a test device and a scanning device. The test device includes a test strip and indicia. The scanning device includes a source of electromagnetic radiation, an optics assembly, a detector, a microprocessor, and a chassis. A feature of the system is that the test device and scanning device are movable relative to each other during operation of the scanning device. In certain embodiments, the test strip includes one or more test lines having immobilized thereto a capture moiety specifically binding directly or indirectly one or more analytes of interest as well as indicia wherein the indicia are positioned on a planar surface of the test device adjacent the one or more test lines.

In another aspect, a method of assaying a sample is disclosed. The method may include one or more of: a) providing a sample to a sample collection device; b) administering the sample from the sample collection device to a test device, c) moving a scanning device across the planar surface of the test device, and d) detecting the analyte of interest. In certain embodiments, the test device may include a lateral flow membrane and indicia. The lateral flow membrane may include one or more test lines having immobilized thereto a capture moiety specifically binding directly or indirectly one or more analytes of interest, as well as indicia, wherein the indicia are positioned on a planar surface of the test device adjacent the one or more test lines. In certain embodiments, the scanning device may include a hand-held chassis, wherein disposed within the hand-held chassis may be one or more of an optical energy source, an optics assembly, an optical energy detector, and/or a microprocessor. A kit including one or more of the test device, scanning device, and/or instructions for using the same is also provided herein.

Additional aspects and features of various embodiments of the invention will be apparent from the following description and appended drawings.

BRIEF DESCRIPTION OF THE DRAWINGS

The present invention may be better understood in conjunction with the appended drawings. According to common practice, the various features of the drawings may not be presented to scale. Rather, the dimensions of the various features may be arbitrarily expanded or reduced for clarity. Included in the drawings are the following figures.

DETAILED DESCRIPTION

Figure 1:
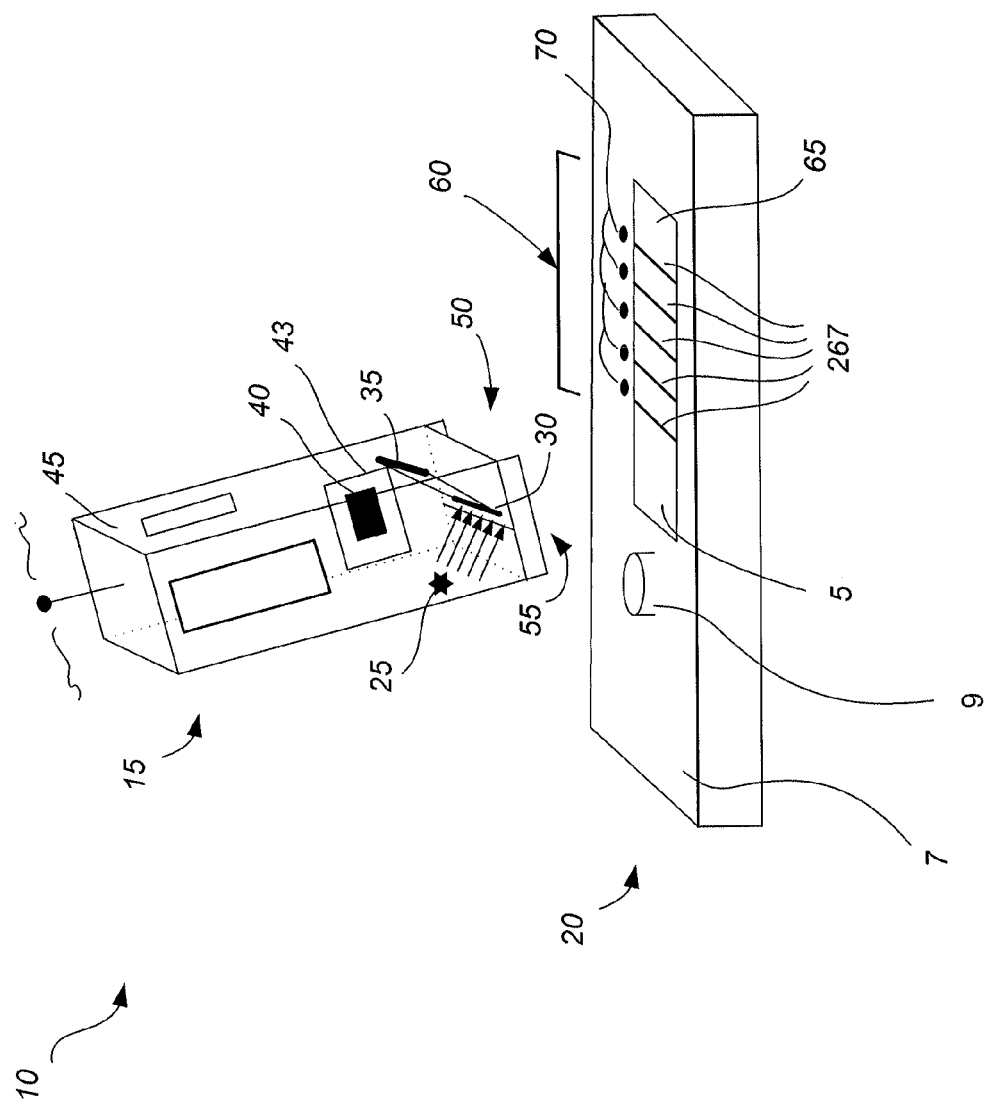
FIG. 1 illustrates a schematic view of an embodiment of a diagnostic system including a scanning device and a test device of the disclosure.

There is a growing need for implementations of hand-held systems including test devices and scanners/readers that enable an operator to easily read and record diagnostic test results. These systems may result in reduced cost and power consumption as compared to current readers, which may more closely approximate the actual point-of-care. In addition, there is a need for readers that can be manufactured inexpensively such that they can be used in a disposable manner or for use, for example, in the third-world. Various embodiments of the present invention may be configured to address these needs as well as others.

Accordingly, disclosed herein are various embodiments of diagnostic assay systems that may include a reader (also denoted herein as a scanner), which may be, configured to be handheld and relatively low cost. The reader may be used for reading test results, such as point-of-care test results from a test device, of a sample, such as a sample obtained from a human or animal patient or from a material or environment under test. The scanner may be configured to be portable, disposable, and easy to use. In certain implementations, the scanner may be configured for use in conjunction with a test device, such as a substrate, with the substrate including one or more indicia serving as a point of reference for the scanning and/or reading of the test device and/or the analyzing and/or outputting of data representative of results obtained by said scanning and/or reading. The substrate may further include one or more test strips for receiving a sample.

In one aspect, a diagnostic assay system is disclosed, comprising: a test device including a test strip having one or more test lines and one or more indicia; and a scanning device comprising: a source of electromagnetic radiation; an optics assembly disposed to direct the electromagnetic radiation; a detector disposed to receive an emission or reflection from the test strip; a microprocessor; and a chassis; wherein the test device and scanning device are configured to be movable relative to each other during operation of the scanning device and wherein the microprocessor is configured to generate test result data based at least in part on the indicia and one or more of the test lines.

In another aspect, a method of assaying a sample to detect an analyte of interest is disclosed, the method comprising the steps of: providing a sample from a sample collection device to a test device, wherein the test device comprises one or more test lines having immobilized thereto a capture moiety specifically binding directly or indirectly one or more analytes of interest, and wherein the indicia are positioned on a surface of the test device adjacent the one or more test lines; moving the test device relative to a scanning device so as to read one or more of the test lines and one or more of the indicia; generating test result data based at least in part on the read of one or more of the indicia and the one or more test lines; and storing the test result data in a memory.

In another aspect, a test device is disclosed, comprising a substrate including: a test strip having one or more test lines; and one or more indicia; wherein the indicia are disposed on the substrate so at to facilitate registration of the test device with respect to a scanner so as to compensate for presentation of the test device to the scanner.

In another aspect, a scanner is disclosed, comprising: a source of electromagnetic radiation; an optics assembly disposed to direct the electromagnetic radiation; a detector disposed to receive an emission or reflection from a test device; a microprocessor; and a chassis; wherein the microprocessor is configured to generate test result data based on one or more indicia associated disposed on the test device and one or more test lines disposed on the test device.

In another aspect, a diagnostic assay system is disclosed. In various embodiments, the diagnostic assay system includes a test device and a scanning device. The test device includes a test strip and indicia. The scanning device includes a source of electromagnetic radiation, an optics assembly, a detector, a microprocessor, and a chassis. A feature of the system is that the test device and scanning device are movable relative to each other during operation of the scanning device. In certain embodiments, the test strip includes one or more test lines having immobilized thereto a capture moiety specifically binding directly or indirectly one or more analytes of interest as well as indicia wherein the indicia are positioned on a planar surface of the test device adjacent the one or more test lines.

In another aspect, a method of assaying a sample is disclosed. The method may include one or more of: a) providing a sample to a sample collection device; b) administering the sample from the sample collection device to a test device, c) moving a scanning device across the planar surface of the test device, and d) detecting the analyte of interest. In certain embodiments, the test device may include a lateral flow membrane and indicia. The lateral flow membrane may include one or more test lines having immobilized thereto a capture moiety specifically binding directly or indirectly one or more analytes of interest, as well as indicia, wherein the indicia are positioned on a planar surface of the test device adjacent the one or more test lines. In certain embodiments, the scanning device may include a hand-held chassis, wherein disposed within the hand-held chassis may be one or more of an optical energy source, an optics assembly, an optical energy detector, and/or a microprocessor. A kit including one or more of the test device, scanning device, and/or instructions for using the same is also provided herein.

Before additional details are further described, it is to be understood that the subject matter described herein is not limited to the particular embodiments described, and as such may of course vary while keeping within the spirit and scope of the present invention. It is also to be understood that the terminology used here in is for the purpose of describing particular exemplary embodiments only, and is not intended to be limiting in any fashion, and in particular with respect to the doctrine of equivalents. Unless defined otherwise, all technical terms used herein have the same meaning as commonly understood by one skilled in the art to which this subject matter belongs.

Where a range of values is provided, it is understood that each intervening value, to the tenth of the unit of the lower limit, unless the context clearly dictates otherwise, between the upper and lower limit of that range, and any other stated or intervening value in that stated range, is encompassed within the subject matter described herein. The upper and lower limits of these smaller ranges may independently be included in the smaller ranges, and are also encompassed within the subject matter described herein, subject to any specifically excluded limit in the stated range. Where the stated range includes one or both of the limits, ranges excluding either or both of those included limits are also included in the subject matter described herein.

It it also noted that, as used herein and in the appended claims, the singular forms "a," "and," and "the" include plural referents unless the context clearly dictates otherwise. Thus, for example, reference to a "fastener" includes a plurality of such fasteners, and reference to "the engagement element" includes reference to one or more engagement elements and equivalents thereof known to those skilled in the art, and so forth.

It is further noted that the claims may be drafted to exclude any optional element. As such, this statement is intended to serve as antecedent basis for use of such exclusive terminology as "solely," "only" and the like, in connection with the recitation of claim elements, or the use of a "negative" limitation. Accordingly, the term "optional" or "optionally present," as in an "optional element" or an "optionally present element," means that the subsequently described element may or may not be present, so that the description includes instances where the element is present and instances where it is not.

As used herein, a "sample" is any material to be tested for the presence and/or concentration of an analyte. In general, the sample may be an environmental, pathological, and/or a biological sample. For instance, in certain instances, the sample is a biological sample. A biological sample can be any sample taken from a subject, e.g., non-human animal or human, which sample, when obtained, may be used in a test device embodiment in accordance with the disclosure herein. For example, a biological sample can be a sample of any physiological and/or body fluid, cells, or tissue samples, such as from a biopsy or other diagnostic test.

Body fluid samples can include, without any limitation: blood, serum, plasma, urine, sputum, feces, semen, cervical mucus, vaginal or urethral secretions, saliva or oral fluid, bile, cerebral fluid, nasal fluid including nasal swab or nasal aspirate, mucous, urogenital swab, spinal fluid, ocular lens fluid, sweat, milk, synovial fluid, peritoneal fluid, transdermal exudates, pharyngeal exudates, bronchioalveolar lavage, tracheal aspirations, cerebrospinal fluid, amniotic fluid, and the like. Herein, fluid homogenates of cellular tissues such as, for example, hair, skin and nail scrapings, and meat extracts are also considered biological fluids, etc. Biological samples can also include any sample derived from a sample taken directly from a subject, e.g., human. For example, a biological sample can be the plasma fraction of a blood sample, serum, protein or nucleic acid extraction of collected cells or tissues. A biological sample can be from any subject, such as an animal, including but not limited to, human, bird, porcine, equine, bovine, murine, cat, dog or sheep.

A biological sample may be untreated or pretreated. Pretreatment of a sample may involve, for example, preparing plasma from blood, diluting or treating viscous fluids, and the like. Methods of treatment of a sample can involve filtration, distillation, separation, concentration, inactivation of interfering components, and the addition of reagents. For example, a biological sample may be a specimen that has been treated in a way to improve the detectability of the specimen or a component within the specimen, such as a virus. For instance, the sample may contain a nasal specimen that includes a virus, which specimen has been treated with a lysis buffer containing a mucolytic agent that breaks down the mucens in the nasal specimen, thereby significantly reducing the viscosity of the specimen, and a detergent to lyse the virus, thereby releasing antigens and making them available for detection by the assay.

Besides physiological fluids, other samples can be used such as environmental, dietary, and/or other samples, such as water, food products, soil extracts, and the like for the performance of industrial, environmental, or food production assays as well as diagnostic assays. In addition, a solid material suspected of containing an analyte of interest can be used as a test sample. For instance, a sample that has been modified to form a liquid medium, or modified to release the analyte may be used. The selection and pretreatment of biological, industrial, and environmental samples prior to testing is well known in the art.

As used herein, the term "exemplary" means "serving as an example, instance, or illustration." Any embodiment described herein as "exemplary" is not necessarily to be construed as preferred or advantageous over other embodiments.

In certain instances, as is described in further detail herein, the devices and methods of the disclosure may be used in the diagnosis of a human. However, the devices and methods disclosed herein may also be useful for the diagnosis of veterinary diseases, analysis of meat, poultry, fish, e.g., for bacterial contamination, inspection of food plants, food grains, fruit, dairy products (processed or unprocessed), as well as the inspection of a given environment, the cleanliness of which is important, such as restaurants, hospitals and other public facilities. For instance, the devices and methods disclosed herein may find use in the analysis of environmental samples, including: water for beach, ocean, lakes or swimming pool contamination. Analytes detected by such tests may include pathogenic agents, such as viral and bacterial antigens, as well as chemicals including, for example, lead, pesticides, hormones, drugs and their metabolites, hydrocarbons, and all kinds of organic or inorganic compounds.

As will be apparent to those of skill in the art upon reading this disclosure, each of the individual embodiments described and illustrated herein has discrete components and features that may be readily separated from or combined with the features of any of the other several embodiments without departing from the spirit and scope of the subject matter described herein. Unless described otherwise, methods recited herein may be carried out in the order of events recited or in other orders that are logically possible. In addition, methods described herein may be performed with more or fewer steps than specifically described in some implementations.

Example Diagnostic Assay System

In one aspect, a system for the performance of a diagnostic assay is described. Embodiments of the system may include a test device and/or a scanning device. For instance, a test device in conjunction with a suitable scanning device can be employed for the purpose of detecting an analyte in a sample. In certain embodiments, a test device and/or scanning device may be provided for use in detecting and therefore determining the presence or absence of an analyte, such as a protein, nucleic acid, and/or small molecule, or the like, in a sample.

In various embodiments, the test device may be any type of device that is capable of retaining a sample and further capable of being scanned by a scanning device, such as a scanning device/reader as described herein. In some embodiments, the test device may include a substrate, and the substrate may further include test strip and/or one or more indicia, such as are described in further detail below. In certain embodiments, the test device may include a housing, with the housing including a lumen that may house the substrate. Additionally, in some embodiments, the substrate and/or housing may be configured for being removably coupled to a sample collection device. In some embodiments, the substrate and/or housing and/or sample collection device may include a bar code and/or text readable indication.

Therefore, in one aspect, the present disclosure is directed to a test device. In general, the test device can include one or more of: an outside housing or casing, a cavity or lumen, defined by the housing, a substrate and/or test strip, such as that described herein below. The outside casing or housing can form the body of the test device and an interior substrate can also be included, wherein the substrate can form a test strip, as described below, which can be present within a lumen of the housing. The body can be made of any suitable material and can include a sample contacting portion and a read results portion. For example, the body of the test device can include a single or a plurality of windows through which a portion, e.g., a read results portion, of a substrate containing a test strip can be exposed.

In certain embodiments where a housing is included, the housing can also include one or more openings and/or windows. For instance, the housing can include a proximal portion having a proximal end and a distal portion having a distal end, wherein an opening can be present e.g., in a proximal end of the device. The opening can be configured for receiving a sample. Thus, the proximal portion of the device can be denoted as the sample receiving portion. In certain embodiments, the opening can be configured for contacting and/or associating with a portion of a sample collection device (SCD), which device may be configured so as to removably couple to the test device, which coupling may allow for the transfer of a sample, contained within the sample collection device, from the SCD to the test device.

Accordingly, in certain embodiments, the opening is positioned above a test strip, with the opening configured such that upon joining with the SCD sample may be transferred to the test device from the SCD and contacted with the test strip. For instance, in certain embodiments, the opening is configured to receive a distal end of a SCD, which distal end may be configured to fit into or onto the opening. In certain embodiments, the test strip includes a wicking material which wicking material may be positioned below the opening, e.g., at a sample contacting portion of the test strip, and which wicking material is configured for receiving the sample when transferred. For example, the opening can be disposed directly above a wicking pad that is disposed downstream of a test pad, which test pad can be positioned at a read results portion of the test strip, as described below.

Furthermore, in some embodiments, a SCD and/or test device, as disclosed herein, can include one or more identifiable tags. In certain instances, the identifiable tags are removable and can be removed from one device and placed on another device. For instance, the test device can include an identity label such as a bar code, which identifies and/or corresponds to an identical identity label on an SCD and can also identify the lot number of the test device (e.g., for quality assurance and tracking purposes).

In certain embodiments, the body of the test device does not include a housing with a lumen. Rather, the test device includes only one or more of a substrate and/or a test strip. As used herein, a test strip refers to the material to which a capture moiety (e.g., nucleic acid, protein, small molecule, metallic particle, nanoparticle, or the like) is linked, e.g., using methods known or developed in the art, and to which at least a portion of the sample may be contacted. Accordingly, in some embodiments, the test device can include a substrate in conjunction with a test strip (which may or may not be contained within the housing of a body) such that together they are configured so as to form a matrix. The matrix may define a flow path, such as an axial flow path. The matrix may include several regions, such as a sample receiving or contacting zone, one or more test zones, and optionally, one or more control zones. In certain embodiments, a test region is included, wherein the test region can include the test and control zones, which can be in the form of addressable lines, as described in greater detail herein below. For example, in certain embodiments, the test device includes a substrate upon which a test strip is associated. The test strip may, for instance, comprise a nitrocellulose membrane, such as a membrane that includes a wicking pad, a test pad, and/or absorbent pad, such as where the wicking pad is proximal to the test pad and configured for receiving a sample, for instance, from a liquid sample collection device, and the absorbent pad may be positioned distal to the wicking and test pad, e.g., where the wicking and absorbent pads are separated by the test pad, and may be configured for absorbing the liquid sample and thereby causing the sample to flow from the wicking pad across the test pad and toward the absorbent pad. It is to be noted, that a wicking and/or absorbent pad may not be included if desired, for instance, a membrane can be provided wherein the membrane is comprised of a single material such as nitrocellulose.

Accordingly, in certain embodiments, a substrate can be provided, which substrate can be associated with one or more of a housing and/or a test strip. A variety of materials can be used as a suitable substrate, including any material that can act as a support for the association of a molecule of interest including, but not limited to organic or inorganic polymers, natural and synthetic polymers, including, but not limited to, agarose, cellulose, nitrocellulose, cellulose acetate, other cellulose derivatives, dextran, dextran derivatives and dextran co-polymers, other polysaccharides, glass, silica gels, gelatin, polyvinyl pyrrolidone (PVP), rayon, nylon, polyethylene, polypropylene, polybutlyene, polycarbonate, polyesters, polyamides, vinyl polymers, polyvinylalcohols, polystyrene and polystyrene copolymers, polystyrene cross-linked with divinylbenzene or the like, acrylic resins, acrylates and acrylic acids, acrylamides, polyacrylamide, polyacrylamide blends, co-polymers of vinyl and acrylamide, methacrylates, methacrylate derivatives and co-polymers, other polymers and co-polymers with various functional groups, latex, butyl rubber and other synthetic rubbers, silicon, glass, paper, natural sponges, insoluble protein, surfactants, red blood cells, metals, metalloids, magnetic materials, or other commercially available media or a complex material composed of a solid or semi-solid substrate coated with materials that improve the hydrophilic property of the test strip, for example, polystyrene, Mylar, polyethylene, polycarbonate, polypropylene, polybutlyene, metals such as aluminum, copper, tin or mixtures of metals coated with dextran, detergents, salts, PVP and/or treated with electrostatic or plasma discharge to add charge to the surface thus imparting a hydrophilic property to the surface.

In certain embodiments, the substrate forms a matrix in the form of a membrane, as described above, wherein the matrix can be self-supporting. Other membranes amenable to non-bibulous flow, such as polyvinyl chloride, polyvinyl acetate, copolymers of vinyl acetate and vinyl chloride, polyamide, polycarbonate, polystyrene, and the like, can also be used. In yet another embodiment, the matrix may form a lateral flow membrane that is composed of a material such as untreated paper, cellulose blends, nitrocellulose, polyester, an acrylonitrile copolymer, and the like. In one embodiment, the test strip substrate is treated with a solution that includes material-blocking and label-stabilizing agents. Blocking agents include bovine serum albumin (BSA), methylated BSA, casein, acid or base hydrolyzed casein, nonfat dry milk, fish gelatin, or similar. Stabilizing agents are readily available and well known in the art, and can be used, for example, to stabilize labeled reagents.

As set forth above, the test device can include a test strip. For instance, the test device can include a substrate, with the substrate including a test strip. A test strip can be a portion of a substrate or can be a membrane or other material that is associated with the substrate and/or housing, in which instance, the substrate can form a backing for the test strip. As used herein in the context of a test device, the terms "test strip," "test membrane" or "lateral flow membrane" may be used interchangeably, dependent on the context.

As indicated, in certain embodiments, the test strip can be a membrane, such as a lateral flow membrane, axial flow membrane, or can be formed as a matrix of one or more materials. In the present context, a lateral flow membrane can be configured so as to employ capillary action or to employ the movement of fluid separate from capillary action, e.g., as where fluid is pumped by the accumulation of gas pressure, hydraulic pressure (direct pumping using a piston or rotary, bellows or other type pump on the assay fluids, electrostatic movement due to an electric field), gravity, etc. to move or transport a sample, such as a test fluid.

Accordingly, the test strip, or a portion thereof, can be composed of one or more of a variety of materials including, but not limited to a lateral flow membrane of a porous material. For instance, in one embodiment, a suitable test strip can be composed of a high density polyethylene sheet, material, such as that manufactured by Porex Technologies Corp. of Fairburn, Ga., USA. The sheet material can have an open pore structure. For instance, the open pore structure can have a density, at 40% void volume, of 0.57 gm/cc and an average pore diameter of 1 to 250 micrometers, the average generally being from 3 to 100 micrometers. In an embodiment the test strip can be a nitrocellulose membrane.

In certain embodiments, the disclosure provides a test device that includes a lateral flow test strip. As described above, the test strip can include one or more zones or pads. For instance, in certain embodiments, the test strip can include a plurality of pads, such as a sample pad, a test pad, and/or an absorption pad. For example, in certain embodiments, a sample pad containing an absorbent material can be included wherein the sample pad is positioned downstream of a test pad. The test strip can additionally include an absorbent pad, containing a wicking material, which absorbent pad can be positioned upstream of the test pad. The lateral flow membrane can additionally include a test pad, which test pad additionally includes a plurality of addressable lines, wherein each line can have immobilized thereto a capture moiety, such as a member of a specific binding pair, e.g., a nucleic acid, protein, or the like, that is capable of binding with a corresponding moiety, such as a binding agent and/or an analyte of interest.

For example, in some embodiments, the test strip can include a test pad or membrane substrate. The test pad can be comprised of a porous material, such as a non-woven, spun-laced acrylic fiber, e.g., New Merge or HDK material. The test pad can itself include one or more zones, such as a test zone and a control zone (such as zones that are useful to verify that the sample flow is as expected). Each of the control zones can include a spatially distinct region that can include an immobilized member of a specific binding pair that reacts with a labeled control reagent. In one embodiment, the control zone can contain an authentic sample containing an analyte of interest, or a fragment thereof. In operation, a labeled reagent can be restrained in each of the one or more control zones. Thus in some embodiments, a test strip and/or substrate of a test device can be a test strip that includes a test membrane that includes 1, 2, 3, 4, 5, 6, 7, 8 or more addressable test and/or control lines.

Upstream of the test membrane substrate can be a wicking substrate. Downstream of the test membrane substrate can be disposed another substrate, such as an absorbent substrate. Suitable materials for manufacturing the absorbent substrate includes but are not limited to, hydrophilic polyethylene materials or pads, acrylic fiber, glass fiber, filter paper or pads, desiccated paper, paper pulp, fabric, and the like. For example, the lateral flow membrane absorbent zone can be comprised of a material such as a non-woven, spun-laced acrylic fiber, i.e., New Merge (available from DuPont) or HDK material (available from HDK Industries, Inc.), non-woven polyethylene treated to improve the hydrophobic property of the material. The test membrane substrate can overlap or abut to one or both the wicking substrate and absorptive substrate, respectively.

Additionally, as set forth above, the test device may include one or more indicia (also denoted herein in plurality as indicias). For instance, the test device can include a test strip and/or substrate, which test strip and/or substrate can include indicia. Indicia can be a marking or label or other form of reference or indication that is capable of being read by a scanner or a component thereof. For instance, the indicia could be a magnetic, electronic or fluorescent marking or label, or the like, that is capable of emitting a signal that is capable of being read be the test device reader or scanner. The emitted signal may be emitted in response to a received illumination, such as a received electromagnetic illumination.

Therefore, in accordance with the devices and methods disclosed herein, a test device can be provided, wherein the test device is configured for being used for the receiving of a sample and for assisting in the detection of an analyte (e.g., a target analyte of interest), present in the sample. In certain embodiments, the test device includes a test strip, which test strip can include a lateral flow membrane that may or may not be associated with a substrate or other backing and may or may not further be housed within a casing or body of the device. The substrate and/or test strip and/or housing may be configured so as to be contacted by a sample and scanned and/or read by a scanning device/reader for detection of an analyte in the sample.

Accordingly, in one aspect, the present disclosure concerns a scanning device/reader. The scanning device can be any suitable scanning and/or reading device so long as it is capable of scanning and/or reading a test device, such as a test device described herein above, and/or detecting the presence or absence of a signal thereon, which signal can be indicative of the presence of one or more analytes in, a sample being tested and/or an indicia positioned on the test device. As used herein, a scanning device refers, generally, to an instrument for detecting and/or quantitating data or emissions, such as on or from test strips or indicia comprised in a test device. The data or emissions may be visible to the naked eye, but does not need to be visible. For instance, in certain embodiments, the scanning device can be a reflectance and/or fluorescent based scanning device and/or text reader configured to detect emissions/reflections in the electromagnetic spectrum or at visible or non-visible light wavelengths. Accordingly, in various embodiments, the scanning device can be a reflectance, transmission, fluorescence, chemo-bioluminescence, magnetic, electromagnetic and/or amperometry scanner (or combinations of two or more of these elements), depending on the signal that is to be detected from the substrate, e.g., of the test device (e.g., LRE Medical, USA). In one embodiment, the scanning device is an ultraviolet (UV) LED scanner that detects a fluorescence signal.

The scanning device can include one or more of a source of energy, such as electromagnetic radiation, an optics assembly, a detector and a microprocessor, each of which may be enclosed in a housing or chassis. In various embodiments, any suitable energy source can be provided. For instance, in certain embodiments, the energy source can be a source of electromagnetic radiation. Any suitable source of electromagnetic radiation can be used in the scanning device so long as the source of electromagnetic radiation is capable of emitting electromagnetic radiation of a type that can be received by a detectable moiety, which detectable moiety is then capable of participating in the generation of a detectable signal, e.g., fluorescence, in response to the received electromagnetic radiation. For example, a suitable energy source can include one or more sources of electromagnetic radiation such as a laser diode, light-emitting diode (LED), an LED array, or flashlamp. The energy source can emit light in the infrared, near infrared, ultraviolet and/or visible wavelengths. The scanning device can additionally include an optics assembly.

The scanning device may also include a detector. Any suitable detector can be used so long as the detector is capable of receiving and detecting an excitation signal that has been generated by a detectable moiety in response to a received signal, such as a signal of electromagnetic radiation. For instance, a suitable detector can be one that is capable of detecting a fluorescence signal, such as a fluorescence signal that is excited by a light emitting diode of a scanning device, which light emitting diode emits a light in the UV region of the optics spectrum and within the absorbance peak of the fluorescence signal (e.g., lanthanide label). For example, a suitable detector can be a photomultiplier tube, photodiode, a PIN photodiode, silicone photodiode, differential photodiode, double diode, fourfold diode, double wedge diode, circular ring diode, photo diode lines, matrix photo diode, PIN array, linear diode array (20-30 diodes), photodiode array (PDA). In certain embodiments, the detector can be a charge-coupled device (CCD), CMOS device, or LED photodiode. In one embodiment, the diode is a UV laser diode. A conventional UV, LED or photodiode can be used.

In some implementations, an imaging chip, such as a CCD or CMOS device, may be used to detect electromagnetic radiation, such as fluorescence, in one or two dimensions. In these implementations, the detector may be configured to provide a signal including a series of two dimensional image frames or one dimensional lines collected from scanning a test sample over time. For example, a test sample may be passed across the sensor and the series of frames or lines sent to a computer module (as further described herein) to determine speed of the sample read, speed variations in the sample presentation, detect and correct for angular offsets in the sample presentation, and/or provide other processing to register or reference the sample, such as in conjunction with indicia, to a reference position or location. The detector may be configured to detect electromagnetic radiation over a range of wavelengths and/or may include a filter or other configuration to limit detection to a discrete wavelength or range of wavelengths.

The scanning device, ay additionally include one or more filters. For instance, where the scanning device is configured for scanning and detecting an emitted fluorescent signal, the emitted fluorescence signal may be detected by a photodiode, with the wavelength of the detected signal then limited using a long pass filter which blocks stray emitted light and accepts light with wavelengths at and around the peak emission wavelength of the fluorescence emitting label. In other embodiments, the long pass filter may be replaced by a band pass filter. Furthermore, the excitation light may be limited by a band pass filter.

The scanning device may additionally include a computer module that may include, for example, one or more embedded microprocessors, microcontrollers, DSP devices, ASICs, FPGAs or other programmable devices (referred to collectively herein as a "microprocessor") and associated memory that may be physically separate from and/or incorporated in the microprocessor. The computer module will generally include one or more memory spaces configured to store instructions for execution on the microprocessor to direct the computer to scan a test sample and determine positional information and/or motion information associated with the sample scan. In addition, the instructions may include instructions for processing the test sample for detection of an analyte, such as is further described below. The microprocessor, as is described in greater detail herein below, can include or be controlled by processor executable instructions comprising data processing software modules, which software modules can employ data reduction and curve fitting algorithms, optionally in combination with a trained neural network for accurately determining the presence and/or concentration of analyte in a biological sample. In addition, the software modules may include instructions to detect position and/or movement information of the sample with respect to the scanner/reader. This detection may be based on detecting sample emissions or reflections as well as emissions or reflections from one or more indicia. The position and/or movement information may be used to adjust or correct the analyte detection results.

Exemplary software modules may include curve fitting algorithms, optionally in combination with software configured for compensating for ambient light and/or other background noise, to determine the presence or amount of an analyte in a given sample. The data obtained from the scanning device then can further be processed by a diagnosis system program or a person capable of reading the output of the data so as to provide a risk assessment or diagnosis of a medical condition as output. In alternative embodiments, the output can be used as input into a subsequent decision support system, such as a neural network, that is trained to evaluate such data. The scanning device may additionally include one or more physical memory devices and/or may include one or more of a receiver for receiving remote commands, e.g., from an external computer, and/or a transmitter for transmitting data, e.g., to an external computer, which data may be transferred wirelessly by a carrier such as an RF frequency, IR radiation, blue-tooth, or the like, or may be transferred using a suitable connector, such as a wire or cable. In certain embodiments, the scanning device may also include a USB port or other communications port for directly associating and/or communicating with an external computer. This may be implemented by incorporating or using external wireless connectivity elements such as IEEE 802.11 (Wi-Fi) component or module, Bluetooth component or module other wireless networking component or module.

As mentioned above, the scanning device may include a suitable housing or chassis. The chassis can be formed of a generally rigid, preferably polymeric material, such as polyvinyl chloride or some other such polymeric material known to those of ordinary skill in the art. In an exemplary embodiment, the chassis can be configured to be of dimensions such that the chassis can be held in a user's hand or placed in a user's pocket. The chassis may include an interface region having a slit or aperture through which energy may be directed, e.g., towards the test device during use. The chassis can include an actual keyboard or a virtual keyboard, for instance, as present on a touch screen display. The keyboard may include a plurality of actuators or keys, including a power on/off key, scan key, cancel key, enter key, alphanumeric keys or other keys on a keypad or touch-screen, and the like. The keys may permit a user to communicate with the instrument as with other hand-held instruments. The housing can include a display, such as an LED or LCD display, and/or a printer. The chassis can include a removable cover that encloses output ports or other data ports and the like. The data port can be configured to accept removable memory devices such as USD drives, SD, memory stick, compact flash or other memory cards, or other similar devices. The chassis can also include an alignment system and/or light shield, such as that surrounding an interface region.

As set forth above, the scanner and/or reader may be configured for interacting with a test strip and/or substrate containing a detectable reaction product of the disclosure and/or an indicia, which test strip and/or substrate can form part of a test device, as described herein. For instance, in one embodiment, the scanner can include a receiving port designed to receive a substrate and/or a test device including a substrate. In certain embodiments, the receiving port may be such that the test device can only be inserted into the receiving port if a depressible (e.g., push button) means upstream of a sample entry aperture has been depressed, thereby allowing the test device to fit into the receiving port in whole or in part. In certain embodiments, the scanner is adapted with a receiving port for a test device. In certain embodiments, the scanner is configured for scanning and/or reading a test strip without physically engaging the test device. Accordingly, in such an implementation, the scanner does not include a receiving port.

Attention is now directed to FIG. 1, which illustrates details of one embodiment of a diagnostic assay system 10 in accordance with the present invention that includes a scanning device 15 and a test device 20, each to be described in more detail below. The test device 20 and the scanning device 15 may be configured so that they can each be hand-held, battery powered, and therefore easily portable. The scanning device 15 can include one or more of an energy emission source, such as a source of electromagnetic radiation 25, an optics assembly 30, a detector 35, and a microprocessor 40 (on a circuit board or other mounting configuration 43, typically accompanied by one or more memory devices and other electronic components (not shown)), and/or a chassis 45, to be described in more detail below. The chassis 45 of the scanning device 15 can be configured to be of dimensions such that the chassis can be held in a user's hand, and can include an interface region 50 that can be positioned near the distal end of the chassis 45. The interface region 50 can include a slit or aperture 55 (also shown in FIG. 4 as 255) through which energy from the energy source 25 can be directed, e.g., towards the test device 20 during use.

The test device 20 can include a substrate 5, which substrate 5 may include a housing 7, an opening configured for receiving a portion of a sample collection device 9, and may further include a diagnostic lane 60. The diagnostic lane 60 may have a test strip 65, to be described in greater detail herein below, and can have adjacent reference marks or indicia 70. The test strip 65 in the diagnostic lane 60 can include bound capture moieties that can interact with analyte in a fluid sample, e.g., obtained from a patient, when contacted with the sample, or portion thereof.

For instance, in an exemplary embodiment, a test strip 65 includes capture moieties that are fixed to the surface of the test strip 65 at predetermined locations. The capture moieties can be configured such that they specifically interact with an analyte, or a portion thereof, in the sample so as to bind thereto and immobilize the analyte at the predetermined locations. In certain instances, the sample has been preprocessed such that any analyte present therein becomes labeled. The presence of the label functions to allow the analyte that has been immobilized at the predetermined location to be detected.

As mentioned above, the substrate 5 may include one or more references marks or indicia 70. The indicia 70, which can be adjacent the diagnostic lane 60, can likewise be read by the scanning device 15 and can act as reference points so as to allow the scanning device 15 to read and interpret the read information. The indicia 70 may be read by the scanning device simultaneously with test lines 267 (further illustrated and described with respect to FIG. 2) in the diagnostic lane 60. The indicia 70 may act as reference points and provide standardization to interpret the orientation of the device thereby to ensure accuracy of the reads. In certain embodiments, an indicia is not a labeled analyte, such as an analyte present in a sample to be read. As shown in FIG. 1, the indicia are in the form of circles or dots, however, in various embodiments they may be provided in different shapes and/or surface features, such as raised textures.

For reading purposes, the scanning device may include a separate channel or use a separate wavelength or detector or processing algorithm in order to interpret a read. As described below, the scanning device can include a separate channel or use a separate wavelength or detector or algorithm in order to interpret and/or otherwise use the data from the test strip(s) and/or indicia 70. In an exemplary embodiment, the relative movement and angle between the test device and the scanner can be standardized and corrected for according to detection of the indicia 70 on the test device and in some instances, a label from an analyte in a test sample to be read. The indicia 70 can also inform the scanning device when a test line in the diagnostic lane 60 is to be read, for example when the scanning device is lined up with each test line in the diagnostic lane 60.

In typical embodiments, the test device 20 can interact with the scanning device 15 in such a manner that the scanning device is able to "read" the test strip 65, detect the labeled and immobilized analyte therein, and thereby provide information about the analyte of interest. The test device 20 and scanning device 15 can be configured such that the two devices are freely movable relative to each other, e.g., in at least one plane. The test device 20 and scanning device 15 can also be configured so as to be freely movable in more than one plane. In some embodiments, the test device 20 need not be inserted into the chassis 45 of the scanning device 15 to accurately read the results of the test device 20. It is noted that in certain instances, the chassis 45 of the scanning device 15 can be configured such that the test device 20 can be received therein. In addition, the chassis 45 may be configured so that the test device 20 may be mechanically aligned and/or locked with the scanning device 15 during reading. However, due to the unique configuration of the present system, this need not be the case.

In conjunction with standardization and correction for the relative movement and angle between the test devices and test samples and the scanners, e.g., via correction software modules as are described herein, there are a variety of ways in which a read can take place. In one embodiment, the test device can be stationary, for example, sitting on a tabletop, and the scanning device can be mobile, for example, held in a user's hand, such that the scanning device is passed across a diagnostic lane and/or indicia of a test device to obtain a reading. In another embodiment, the scanning device may be stationary and the test device may be mobile, for example, held in a user's hand, such that the test device is passed in front of an interface region of the scanning device to obtain a reading. In another embodiment, both the test device and the scanning device can be mobile, for example each may be held in a user's hands during a reading. The relative movement and angles between the test device and the scanning device may be standardized and corrected for according to detection of the indicia and/or label on the test device and/or the test strips, and calculations made by a software algorithm or algorithms implemented in one or more software modules.

Example Test Device

As described above, the disclosed diagnostic assay system may include a test device and a scanning device, which devices may be used in conjunction with one another so as to detect one or more analytes of interest in a sample, which sample can be processed by the test device and which analyte can be detected by the scanning device. In some implementations, the test device and scanning device may be provided as separate embodiments, each configured to provide at least part of their corresponding functionality as described herein.

Figure 2A:
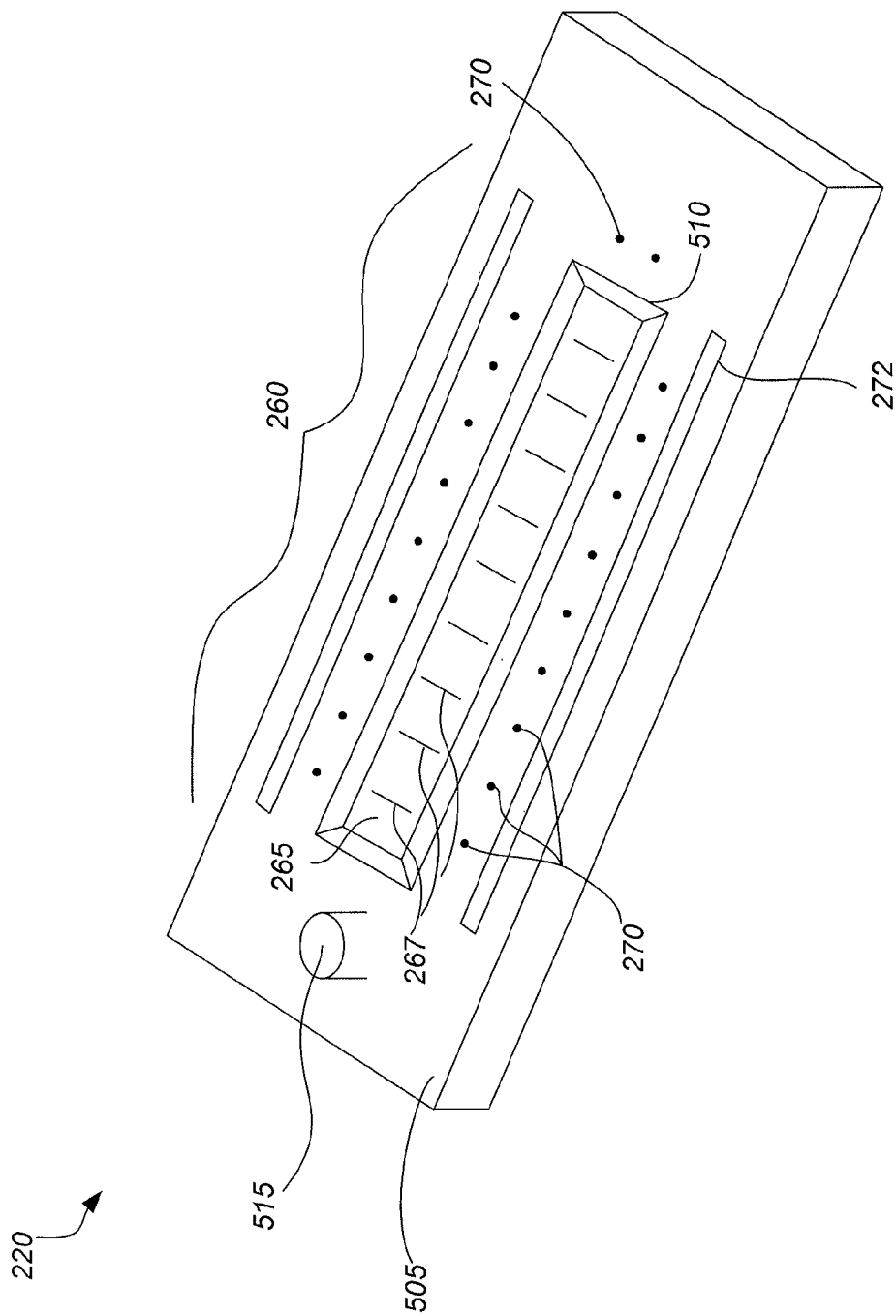
FIG. 2A illustrates an embodiment of a test device.

Turning to FIG. 2A, one embodiment of the test device 220 may include a test strip 265 having one or more test lines, dots or other shapes 267. The test lines 267 may be areas in which a capture moiety is bound such that analyte of interest can be captured and "read" with the scanning devices described herein.

As used herein in the context of a test device, the terms "test strip" or "test membrane" or "lateral flow membrane" are used interchangeably. The test strip 265 can be a lateral flow membrane, axial flow membrane, or matrix. In an embodiment, the test strip 265 may be a nitrocellulose membrane. The test device 220 may include a substrate with a housing or other body 505 or a material with which the test strip 265 is associated. The test strip 265 can include a capture moiety, which capture moiety can be linked to the test strip at a predetermined position using methods known in the art.

For instance, in one embodiment, the test device 220 may include a test strip 265 disposed within a housing or body of a substrate 505 (see, for example, FIG. 2A). The body 505 can include a window 510 or plurality of windows near the diagnostic lane 260 through which the test strip 265 is exposed. The body 505 can also include a port or opening 515 to which a sample collection device can be affixed and sample delivered to the test device 220 for analysis. It should be appreciated that the test device 220 need not include a body 505. The body 505 of the test device may be composed of rigid or semi-rigid, non-water-permeable material such as glass, ceramic, metal, plastic, polymer, copolymer or combinations thereof. The body 505 can also function as an adapter for reading a test strip 265 directly with the scanning device.

As mentioned above, the body 505 of the test device 220 can include features that can interface with a scanning device, such as a scanning device described herein below. For example, as can be seen with respect to FIG. 2B, if the scanning device 215 includes an alignment system 257, the body 505 of the test device can have complementary alignment features 272 that interface with the alignment system 257 of the scanning device. As best shown in FIGS. 2A-2D, the alignment system 257 of the scanning device can be, for example, a pair of parallel rails positioned on either end of the aperture 255 near the interface region 250 (see FIG. 4) of the device 215. Such an alignment system 257 can, for example, slideably interface with corresponding alignment features 272 present on the surface of the test device 220. The alignment features 272 of the test device 220 can be, for example, a pair of longitudinal channels. Alternatively, the alignment features 272 of the test device 220 can include raised tracks over which the alignment features 272 of the scanning device 215 are guided during a swipe (see FIG. 2D). The configuration of the alignment system 257 and corresponding alignment features 272 can vary. It should also be appreciated that the scanning devices described herein and the test device need not mechanically couple. Even if an alignment system 257 is incorporated in the scanning device, the test device and scanning device may be independently and freely movable relative to each other.

As described above, the body 505 or test strip 265 may include reference marks or indicia 270 positioned adjacent the diagnostic lane 260. As set forth above, such indicia may be detectable independently from a labeled analyte within a sample to be read. The indicia 270, however, may likewise be read by the scanning device, such as simultaneously with the test lines 267, and may act as reference points and provide standardization to interpret the orientation of the read direction and so as to ensure the accuracy of the read(s). The indicia may also be used to correct for variation in presentation angle and/or sample speed with respect to the scanner.

As described below, the scanning device can include a separate channel or use a separate wavelength or detector or algorithm in order to interpret and/or otherwise use the data or emissions from the indicia 270. Accordingly, the relative movement and angle between the test device and the scanner can be standardized and corrected for according to detection of the indicia 270 on the test device. The indicia 270 can also inform the scanning device when a test line 267 is to be read, for example when the scanning device is lined up with each test line 267.

The indicia 270 can be printed directly on the test device 220, integral with the test strip 265 or attached to the device such as by removable stick-on labels. The indicia 270 can form a pattern. For example, the pattern can be in 1, 2 or 3 dimensions. The pattern may be used to correlate the indicia readings in the scanner with a known reference pattern so at to adjust the read data responsive to the correlation. This may be done in a software module of the scanner in conjunction with a microprocessor, such as microprocessor 40.

In one embodiment, the indicia 270 can be a labeled reference point such as a Europium label or other detectable label. The indicia 270 can be in gray scale or in color. In one embodiment, the indicia 270 form a two-color pattern. The indicia 270 can also be raised bumps, indentations, or metal electrodes in the body 505, which be detected mechanically or electrically with the scanning device 215. For example, the scanning device 215 can have electrodes on one or more sides that come in contact with the electrodes serving as the indicia 270. Alternatively, the scanning device 215 can have hinged or bendable flaps extending downward from its bottom side, which deflect as they pass over the bumps serving as the indicia 270 or which move downward as they pass over the indentations serving as the indicia 270. Such flaps can be connected to leads, which can carry an electrical signal as the flaps deflect or move in a certain direction.

Figure 3:
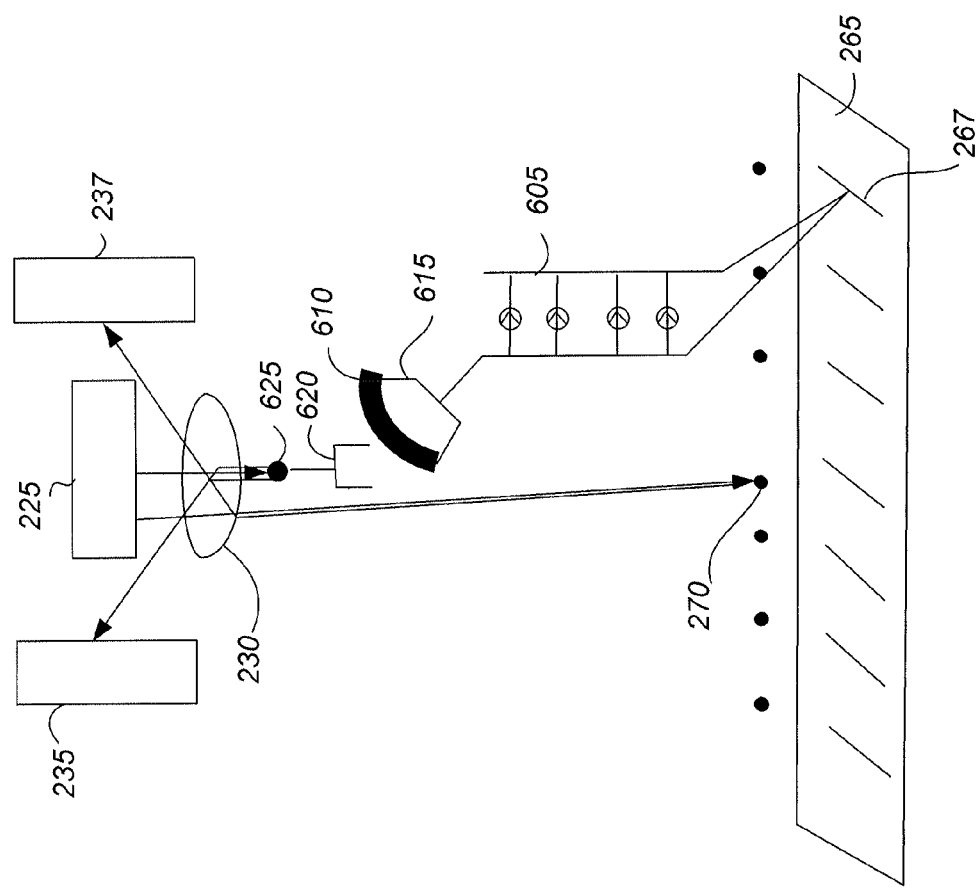
FIG. 3 illustrates a schematic view of an example of the detection of an analyte using an embodiment of the diagnostic system.

As shown in the schematic of FIG. 3, the test strip 265 within the diagnostic lane 260 can include one or more test lines 267. The test lines 267 may be areas to which a capture moiety 605 is immobilized for capturing an analyte of interest 610 from a fluid sample. The capture moiety 605 binds either directly or indirectly to the one or more analytes of interest 610 from the fluid sample. Indirect binding such as through sandwich immunoassay techniques as known or developed in the art can be incorporated. Indirect binding of an analyte of interest 610 involves the use of a binding agent such as a capture antibody or capture probe 615 that is immobilized on the capture moiety 605. A detection probe 620 refers to a binding agent that captures an analyte of interest in the fluid sample and is linked to a detectable label 625, moiety or signal producing moiety. The capture probe 615 and detection probe 620 are each capable of specifically binding to a target analyte 610.

The test strip 265 can also include a control line or spot (not shown). The control line can confirm that a sufficient amount of capture moieties 605 could react with the corresponding capture probe 615 complexed to a specific analyte 610. Control reagents can confirm that the immunocomplexes migrate onto the diagnostic lane 260 and cross the test line 267 in an amount that the accumulation of labeled analyte 610 would produce a visible or otherwise readable signal in the case of a positive test result.

Capture moiety 605 can include one or more of a binding pair as known in the art such as avidin and/or streptavidin, as well as pyranosyl RNA (pRNA), oligonucleotide, aptamer, modified nucleic acid, nucleic acid pyranosyl-RNA sequence, nanoparticle, polypeptide, protein, antibody or combination thereof (see PCT Publication Nos. WO07098184 and WO09014787, which are incorporated herein by reference in their entirety, for examples of binding pairs, capture moieties, and labels). Additional capture moieties or combination of capture moieties can be used as are known in the art. Accordingly, capture probe 615 and detection probe 620 can include antibodies, aptamers, oligonucleotides, and the like. Additional probes or combination of probes'can be used as is known in the art.

The label 625 can be any substance capable of producing a signal that is detectable by visual or instrumental means. Exemplary labels 625 can include enzymes, substrates, chromagens, catalysts, fluorescent or fluorescent-like compounds and/or particles, magnetic compounds and/or particles chemiluminescent compounds and/or particles, and radioactive labels. Other suitable labels include particulate labels such as colloidal metallic particles such as gold, colloidal non-metallic particles such as selenium or tellurium, dyed or colored particles such as a dyed plastic or a stained microorganism, organic polymer latex particles and liposomes, colored beads, polymer microcapsules, sacs, erythrocytes, erythrocyte ghosts, or other vesicles containing directly visible substances, metals, fluorophores, chromophores, Europium or any combination thereof. Additional labels or combination of labels can be used as are known or developed in the art.

Target analytes of interest to be assayed by the system disclosed herein can vary. As used herein the term "analyte" or "analytes" refers to the compound or composition to be detected or measured and which has at least one epitope or binding site. The analyte can be any substance for which there exists a naturally-occurring or synthetic analyte-specific binding member or for which an analyte-specific binding member can be prepared, e.g., carbohydrate and lectin, hormone and receptor, complementary nucleic acids, and the like. Further, possible analytes include virtually any compound, composition, aggregation, or other substance which can be immunologically-detected. That is, the analyte, or portion thereof, may be antigenic or haptenic having at least one determinant site, or will be a member of a naturally occurring binding pair. In other embodiments, one or more analyte detected is an antibody (e.g., IgG, IgM) in a sample (e.g., urine, oral fluid, blood, plasma or serum sample) where the antibody is specific for a virus or virus component, bacteria or bacteria component, cancer cell or tumor antigen. For example, by detecting one or more antibody, the assay indicates that the patient has been previously infected by an infectious agent or suffers an underlying condition with which the antibody is associated. In further embodiments, allergy detection testing comprises detecting the presence of specific IgG, IgM and/or IgE Ab in a subjects oral fluid, whole blood, urine, plasma or serum to specific allergens.

Analytes of interest can include toxins, organic compounds, proteins, peptides, microorganisms, bacteria, viruses, yeast, fungus, parasites, cancer cell, amino acids, nucleic acids, modified nucleic acids, polypeptides, proteins, antibody, derived from an infectious agent, carbohydrates, hormones, steroids, vitamins, drugs (including those administered for therapeutic purposes as well as those administered for illicit purposes), pollutants, pesticides, and metabolites of or antibodies to any of the above substances, antigenic substances, haptens, macromolecules, and combinations thereof. Other analytes of interest can include Influenza A, influenza B, seasonal influenza subtypes (H1N1 and H3N2), and pandemic influenza subtype H5N1, BNP, NT-proBNP, proBNP, CNP, ANP, RSV, adenovirus, upper respiratory infection panel, *Streptococcus pneumoniae*, mycoplasma pneumonia, HIV, HCV antigens, tuberculosis, SARS-associated coronavirus, hepatitis panel comprising a selection of hepatitis B surface Ag or Ab, hepatitis B core Ab, hepatitis A virus Ab, and hepatitis C virus; a phospholipids panel comprising a selection of Anticardiolipin Abs (IgG, IgA, and IgM Isotypes); an arthritis panel comprising a selection of rheumatoid factor, 15 antinuclear antibodies, and Uric Acid; an Epstein Barr panel comprising a selection of Epstein Barr Nuclear Ag, Epstein Barr Viral Capsid Ag, and Epstein Barr Virus, Early Antigen; other panels include HIV panels, Lupus panels, H. Pylon panels, toxoplasma panels, herpes panels, *Borrelia* panels, *rubella* panels, cytomegalovirus panels, panels testing for recent myocardial infarction or congestive heart failure, such as analytes comprising an isotype of troponin, myoglobin, natriuretic peptide (e.g., ANP, pro-ANP, BNP, pro-BNP, CNP, NT-proBNP, etc.), D-dimer, and/or CKMB, one or more virus or virus components, one or more bacterial or bacterial components, one or more cancer cell or cancer cell components, one or more analytes associated with a condition such as a brain condition, damage or disease, heart condition, damage or disease, cancer or neoplastic condition, or disease, liver condition, damage or disease, kidney condition, damage or disease, or a combination thereof.

In various embodiments, the analyte(s) detected are associated with an infectious agent. An infectious agent can be any pathogen including without any limitation bacteria, yeast, fungi, virus, eukaryotic parasites, etc. In some embodiments, the infectious agent is influenza virus, parainfluenza virus, adenovirus, rhovirus, coronavirus, hepatitis viruses A, B, C, D, E, etc, HIV, enterovirus, papillomavirus, coxsackievirus, herpes simplex virus, or Epstein-Barr virus. In other embodiments, the infectious agent is *Mycobacterium, Streptococcus, Salmonella, Shigella, Staphylcoccus, Neisseria, Clostridium*, or *E. coli*. It will be apparent to one of skill in the art that different infectious agents can be detected using a different panel of binding agents (e.g., antibodies) that are specific for type(s) or subtype(s) of an infectious agent(s).

Example Scanning Device

Figure 4:
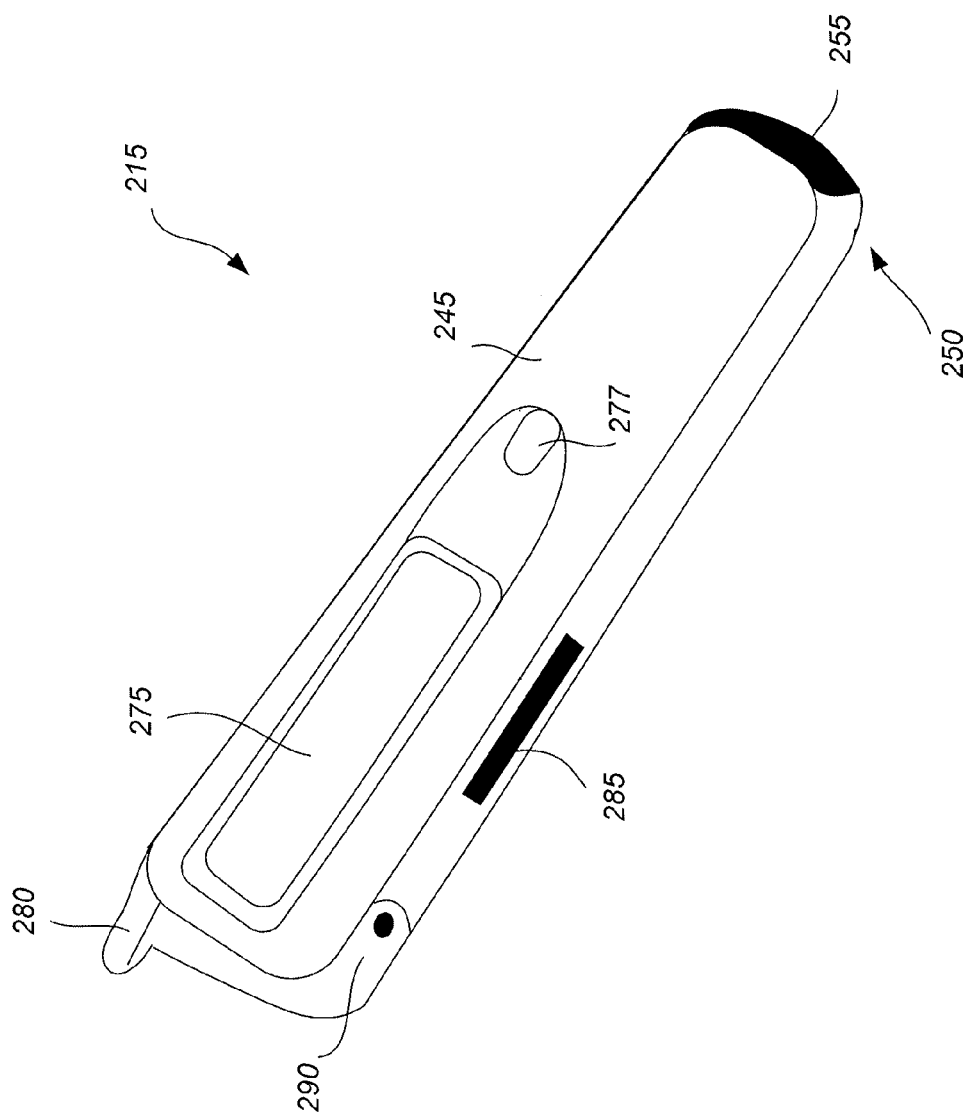
FIG. 4 illustrates an embodiment of a scanning device.
Figure 5:
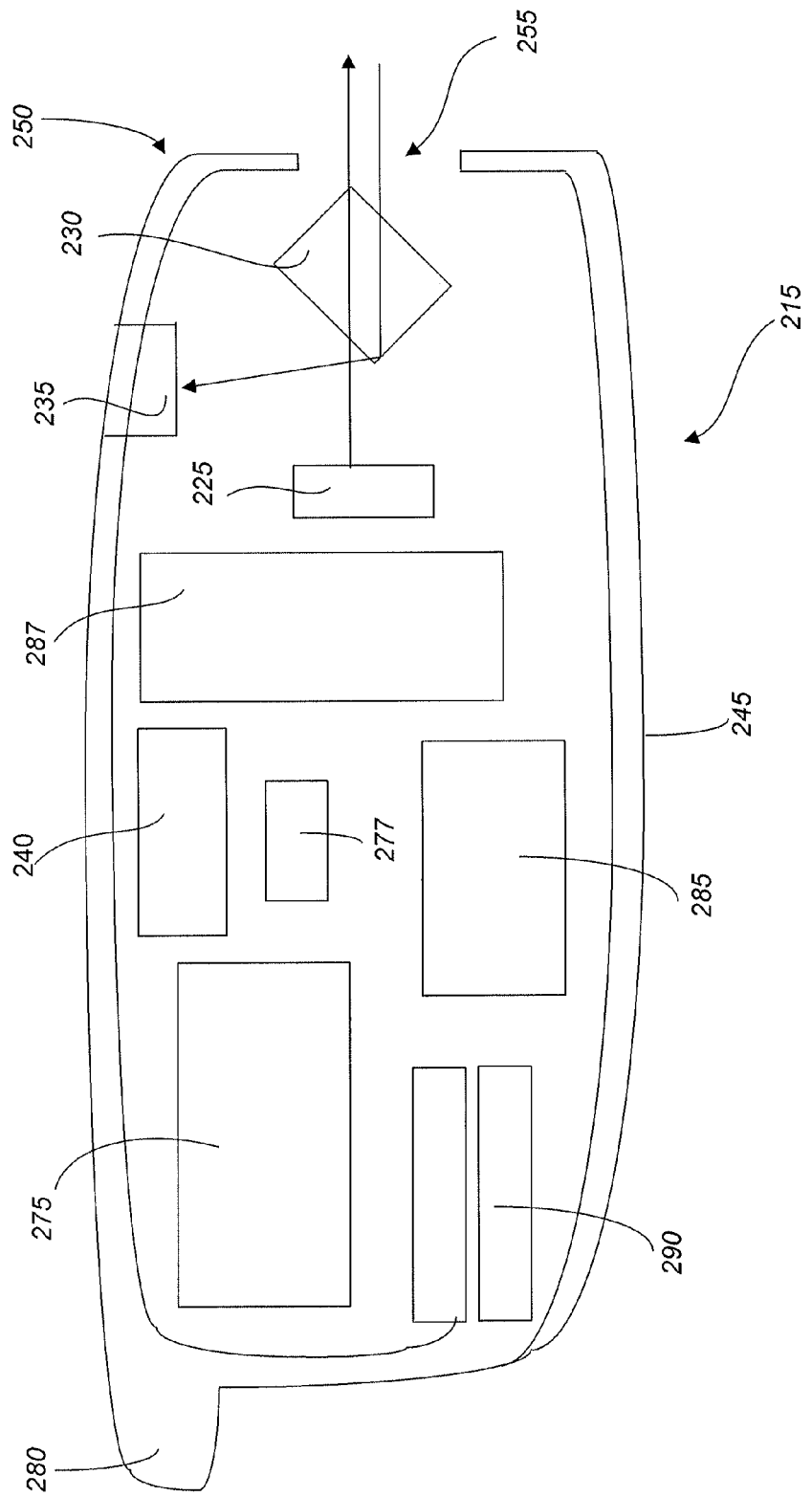
FIG. 5 illustrates a schematic view of the scanning device of FIG. 4.

FIGS. 4 and 5 illustrate an exemplary embodiment of a scanning device 215. As mentioned above, the scanning device 215 may include an energy emission source 225, an optics assembly 230, a detector 235, and a microprocessor 240 and associated memory, each disposed within a chassis 245. The scanning device 215 may be configured so as to be easily portable, may be battery powered, may be capable of being held in a user's hand and may be small enough to be placed in a user's pocket. Near the distal portion of the chassis 245 is an interface region 250 having an aperture 255 through which the scanning device 215 reads a test device containing a diagnostic lane, as described in more detail below. To perform a reading of a test device, the chassis 245 is swept over the diagnostic lane of the test device with the interface region 250 pointed towards the diagnostic lane. The chassis 245 of the scanning device 215 may be configured to be freely moved by the user with respect to the test device and vice versa. In certain embodiments, the test device is not inserted or loaded into the chassis 245 of the scanning device 215.

The scanning device 215 may include one or more energy emission sources 225 such as an electromagnetic radiation source that emits light to excite a labeled sample immobilized at a test line 267 of the test strip 265. The energy source 225 can include one or more sources of electromagnetic radiation such as for example a laser diode, light-emitting diode (LED), an LED array, a flashlamp, and/or other sources as are known or developed in the art. The energy source 225 can emit light, for instance, in the infrared, near infrared, ultraviolet and visible wavelengths. The light emitted by the source 225 can be tuned to a specific frequency or range of frequencies or set of frequencies or ranges of frequencies. In an embodiment, the device 215 includes a plurality of energy sources 225. In a further embodiment, the device 215 includes an array of energy sources 225.

The scanning device 215 may also include one or more detectors 235. The detector 235 may be configured to detect, capture and/or sense light, fluorescence or other electromagnetic energy reflected or emitted from the direction of the diagnostic lane 60 of the device 215 and provide a corresponding output signal. For example, the detector 235 can detect light emitted from a labeled analyte in response to excitation energy from the energy source 225. The detector 235 can be optimized such that it detects for example, Europium or another label. In one embodiment, the device 215 includes a plurality of detectors. In a further embodiment, the device 215 includes an array of detectors.

The detector 235 can be a photomultiplier tube, photodiode, a PIN photodiode, silicone photodiode, differential photodiode, double diode, fourfold diode, double wedge diode, circular ring diode, photo diode lines, matrix photo diode, PIN array, linear diode array (20-30 diodes), photodiode array (PDA). In an embodiment, the detector 235 can be a charge-coupled device (CCD), CMOS' device or LED photodiode. This type of detector employs an array of tens, hundreds or thousands of tiny light sensors lined up in a row. Each sensor can measure the intensity of the light and generates a voltage pattern. Such sensors can measure the emitted ambient light from the test device instead of measuring reflected light of a specific frequency originating from the energy source. In one embodiment, the detector 235 can employ 2-dimensional imaging for example using a small video camera to capture images. This type of imaging can use CCD technology or CMOS sensors. Instead of a single row of sensors (i.e., one-dimensional detector), a two-dimensional array of sensors may be employed. This detector configuration may provide a series of two dimensional frames or one dimensional lines that can be provided to the microprocessor to determine position or registration as well as movement so as to correct the alignment of the test sample for angle and/or movement.

Figure 2B:
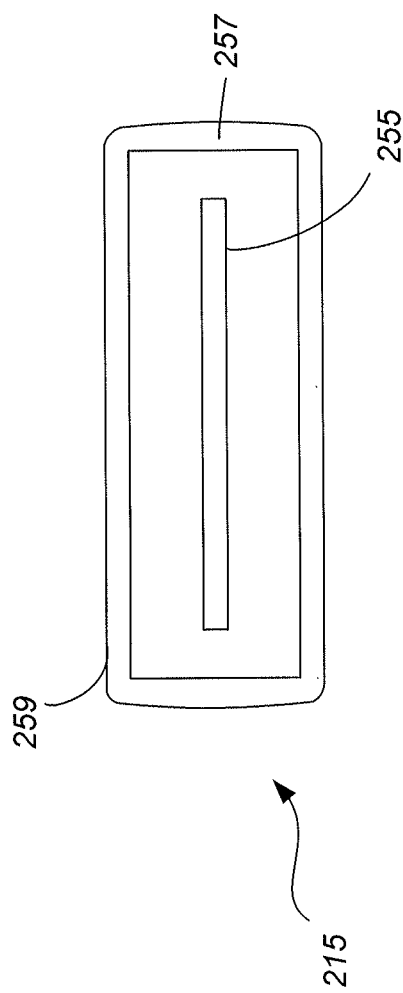
FIG. 2B is a distal end view of an embodiment of a scanning device having an alignment system and light shield attached near the test device interface region.
Figure 2C:
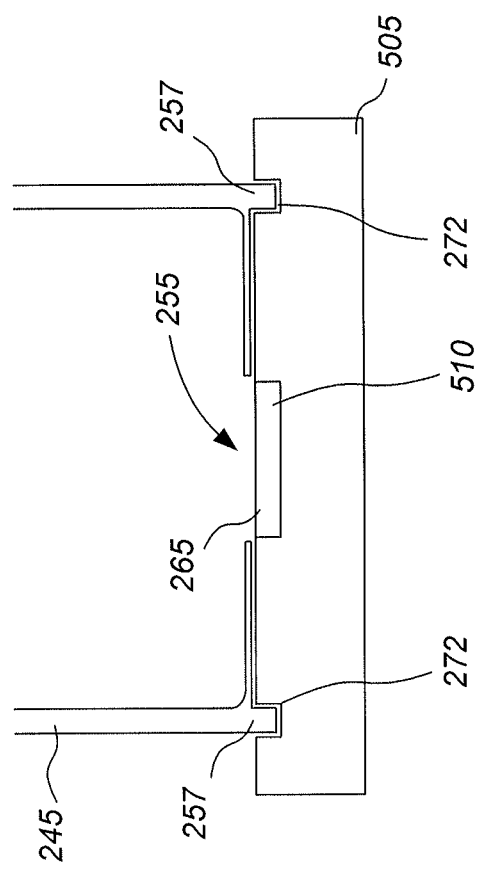
FIG. 2C is a cross sectional view of the interface between the test device of FIG. 2A and the scanning device of FIG. 2B.
Figure 2D:
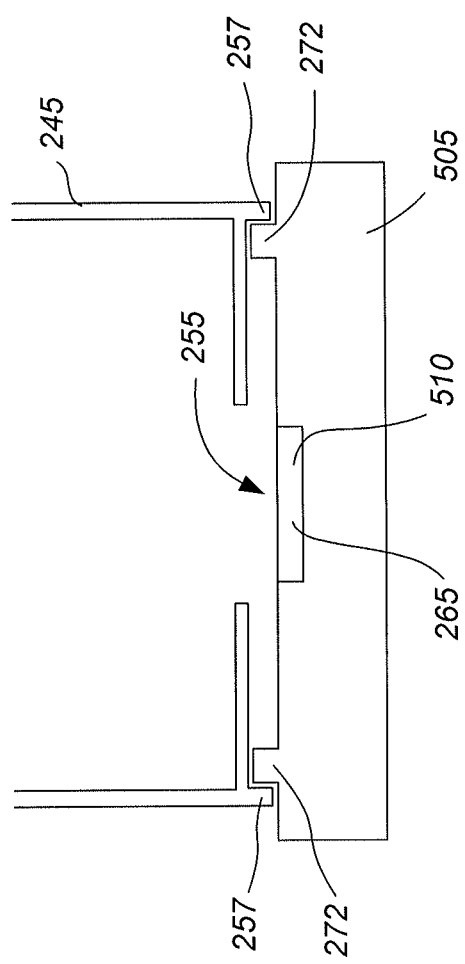
FIG. 2D is a cross-sectional view of another embodiment of an interface between a test device and a scanning device.
Figure 7:
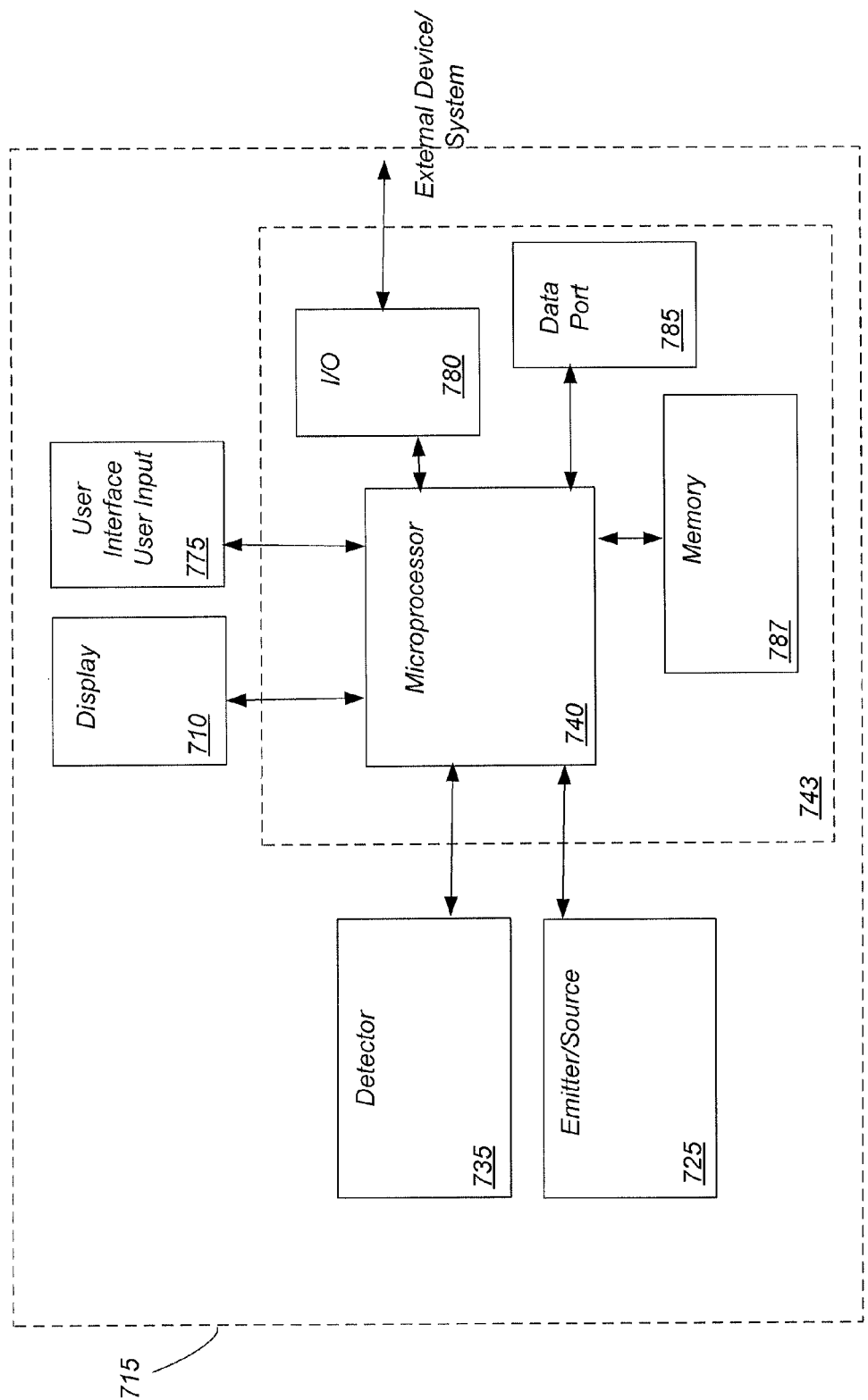
FIG. 7 illustrates an embodiment of a microprocessor subsystem for use in a scanning device.

FIG. 7 illustrates additional details of an embodiment of a device 715 and associated electronics elements. Device 715 may correspond with devices 15 and 215 as shown in FIGS. 1 and 2B. As shown in FIG. 7, a circuit board or other similar or equivalent structure 743 incorporating electronics may include a microprocessor 740 (which may correspond to microprocessors 40 and 240 of FIGS. 1 and 2A), one or more memory devices 750, one or more input/output (I/O) devices 730, as well as other electronic elements (not shown for purposes of clarity) as are known in the art. In general, the microprocessor 740 is communicatively coupled to memory 787, which may be configured to store instructions comprising one or more software modules, as well as sample data, user input(s), output data, and/or other associated data or information. I/O module 780 may be configured to electronically couple device 715 with external devices, such as external computers or other systems as are described herein. I/O module 780 may include a serial or parallel communication element (such as a USB module, firewire module or other like module), a wireless communications module (such as a Wi-Fi, Bluetooth or other wireless module), an optical I/O module, or other communications module as is known or developed in the art. Device 716 may include one or more data ports 785, configured to receive memory storage devices such as USB devices, SD, CompactFlash, memory stick or other devices.

In addition, device 715 may include one or more display modules 710, such as LEDs, LCDs or other display or indication modules and one or more user input modules 775, such as pushbuttons, keypads, mice and the like to receive user inputs. In addition, device 715 may include one or more detector modules 735, which may correspond with detectors 35 and 235, as well as one or more emitter/source modules 725, which may correspond with sources 25 and 225.

Figure 6:
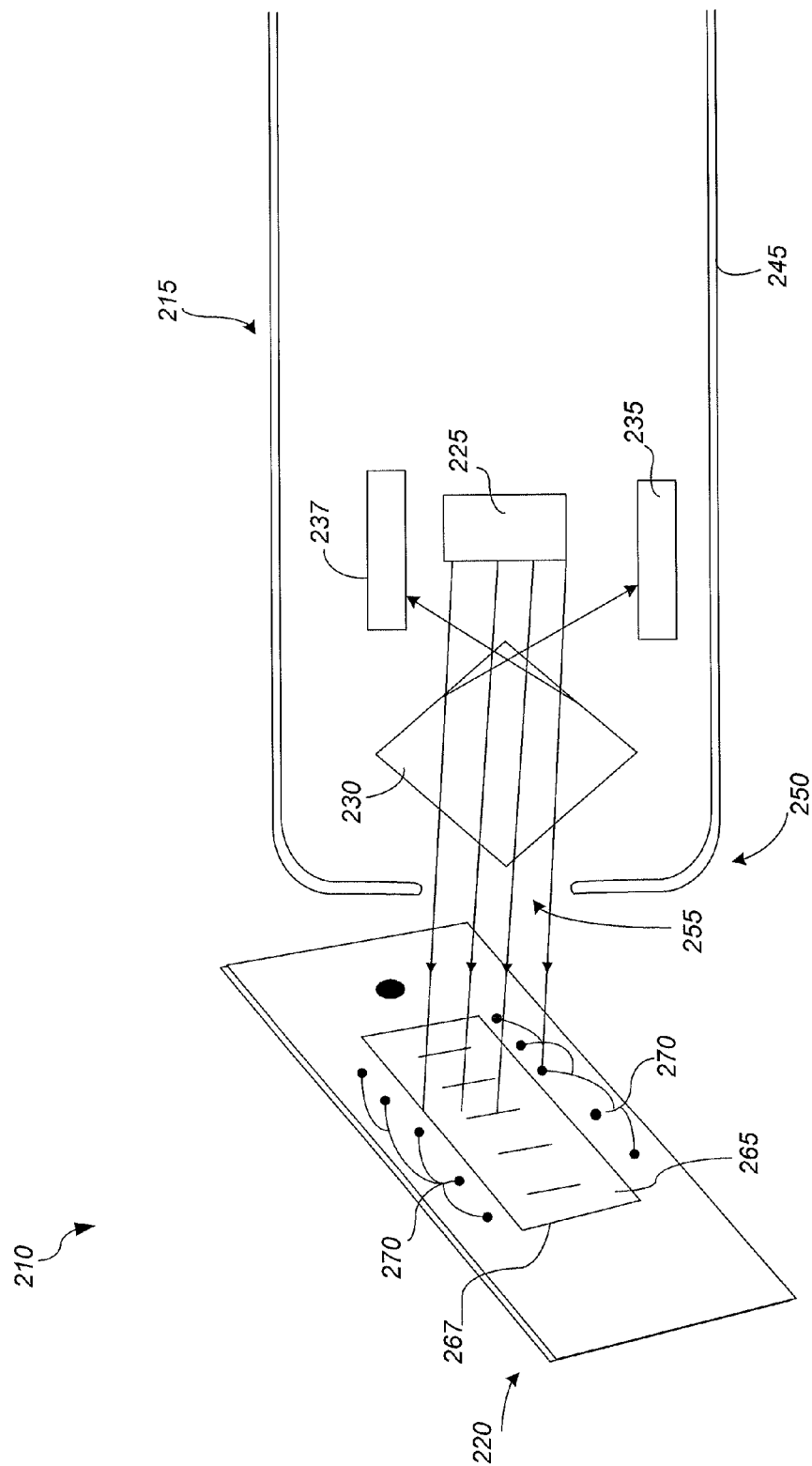
FIG. 6 illustrates a schematic view of the optics assembly of an embodiment of a scanning device.

Attention is now directed to FIG. 6, which illustrates additional details of some embodiments. As shown in FIG. 6, in some embodiments the device 215 may include two (or more) detectors 235, 237. The detectors 235, 237 can detect different wavelengths of ranges of wavelengths of energy. In one embodiment, detector 235 detects wavelengths in the range of, for instance, in the infrared, near infrared, ultraviolet and visible wavelengths. In one embodiment, the wavelengths detected by detectors 235 and 237 are sufficiently different from the wavelength of excitation light emitted from the energy source 225 so as to reduce background noise. In one embodiment, detector 235 detects wavelengths from a labeled analyte of interest immobilized on the test strip 265 of the test device 220 and detector 237 detects wavelengths from indicia 270 on the test device 220. The detectors 235, 237 may be configured to detect wavelengths from the labeled analyte as well as wavelengths from the indicia 270 in a single pass of the chassis 245 over the diagnostic lane 260. It is to be noted that although in this embodiment one detector, e.g., 235, detects a wavelength of energy emitted from a label in its excited form, and another detector, e.g., 237, detects a wavelength of energy emitted from the indicia, in some embodiments, a single detector can be configured for receiving and detecting both a wavelength of energy emitted from the label as well as a wavelength of energy emitted from the indicia.

Depending on the label used, the excitable energy emitted from the energy source 225 is at a wavelength that differs from the emitted energy from the sample excited such that background signals measured by a detector will be minimized. To further improve the signal-to-background ratio of the system, one or more filters can be included such as high-pass filters to cutoff frequencies of the energy source at frequencies below (wavelengths above) the preferred excitation wavelength that could potentially be a source of background for the detector. A low-pass filter can also be included to cutoff frequencies of the energy source at frequencies above (wavelengths below) the preferred detection frequency.

It should be appreciated that the scanning devices described herein can include additional energy sources and additional detectors or other combinations of energy sources and detectors. For example, a detector may be included that detects other labels from the test device such as for example barcodes, radio frequency emitters, light energy emitters, electromagnetic wave emitters, magnetic strips, an inductive circuit or a combination thereof. The information provided by such labels may include for example, patient identification, sample identification, sample type, identification of a test to be performed on a sample, or a combination thereof.

As shown in FIG. 6, the scanning device 215 includes an optics assembly 230. The optics assembly 230 may be configured to direct the energy from the energy source 225 towards a test device 220 through the aperture 255 in the interface region 250 of the chassis 245. The energy passing through the optics assembly 230 is spread over the diagnostic lane 260 of the test device 220 such that test lines 267 as well as indicia 270 on the test device 220 are energized. A reflectance read as well as a fluorescence read may be performed simultaneously in a single pass of the scanning device across the test device.

The optics assembly 230 may include one or more filters, lenses, mirrors and the like. The energy may be directed by the optics assembly 230 at an axis that, in certain embodiments, may be at least about a 90 degree angle relative to the test device. In one embodiment, the energy emitted from the energy source 225 is directed to the test device at approximately a 45 degree angle. Other angles and alternative configurations may also be used in various embodiments.

The energy source 225 may be positioned such that energy is emitted toward the test device at a specific angle. In one embodiment, the source 225 may be positioned at a 90 degree angle to the test device. In other embodiments, the source 225 may be positioned at an angle that is more or less than a 90 degree angle with respect to the test device. Similarly, the one or more detectors 235 may receive light from the labeled analyte and/or the indicia on the test device at a specific angle, for example, an angle more or less than or equal to 90 degrees relative to the test device.

Filters may be included as part of the optics assembly 230, for example cut-off or band-pass filters to reduce background. If the energy source provides excitation energy at a particular wavelength, the emitted wavelength may be sufficiently different from the excitation wavelength to reduce background.

Turning again to FIG. 5, the detector 235 communicates the detected optical signals to the microprocessor 240. The microprocessor 240 processes the data from the detector 235 into a response or output signal. The microprocessor 240 is configured to run one or more software modules that may include data reduction and curve-fitting algorithms such that relative movement between the test device and the chassis 245 of the scanning device 215 during a read may be detected, compensated and corrected. For example, corrections can be made for variable speed and dwell time on any particular location of the test device. The angle or relative alignment between the detector 235 and the test device 220 can also be corrected. Corrections may be made in one or more planes including, for example x-, y- and z-planes.

Figure 8:
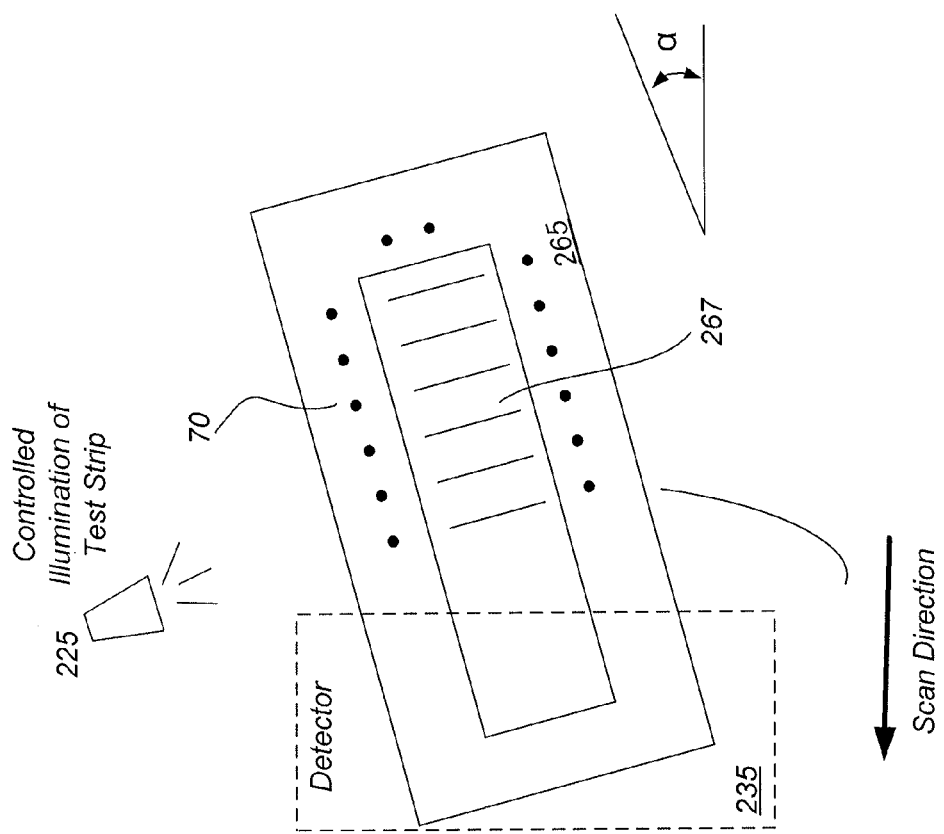
FIG. 8 illustrates details of test sample scanning using a detector in accordance with aspects of the present invention.

FIG. 8 illustrates details of reading a test sample on a test strip 265 that includes indicia and test lines as shown in FIG. 1. The test strip 265 is positioned as described previously herein so that it may be passed by the detector(s) 235, typically via linear motion in the scan direction. The test strip may be illuminated by a source as described previously herein, such as source 225, so as to emit or reflect electromagnetic radiation that may then be detected by the detector element. In FIG. 8, the test strip is offset at an angle $\alpha$ with respect to the detector; however, by determining the relative positions of the indicias 70, the corresponding alignment of the test strip with respect to detector 235 (and the associated scanner/reader) may be determined by processing the detected indicia and/or test lines 267. In addition, speed may likewise be determined by processing the detected indicia and/or test lines and calculating, based on known parameters such as indicia and/or test line spacing, the relative speed and/or speed variations in presenting the sample.

Figure 9:
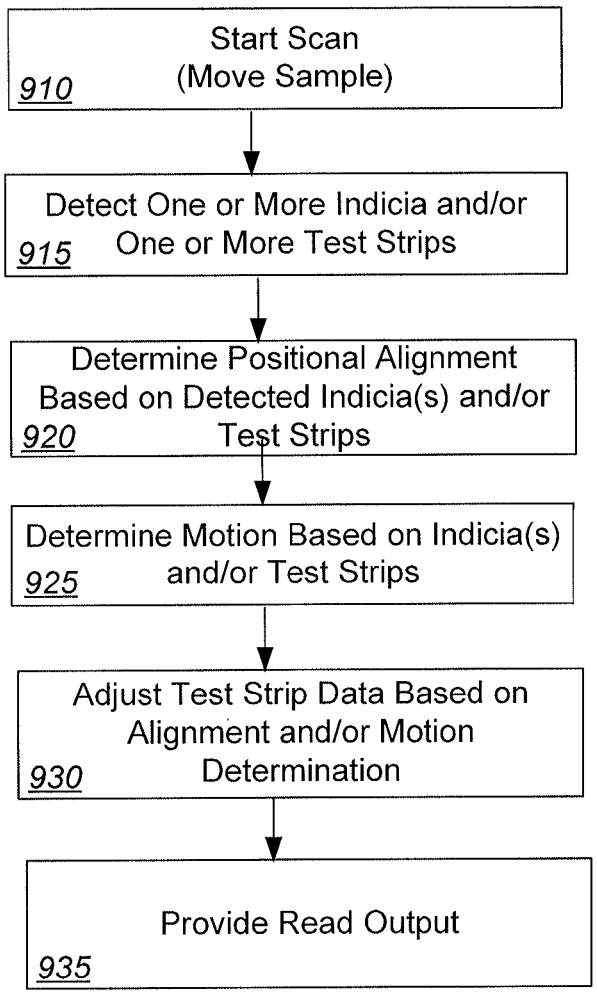
FIG. 9 illustrates a process for scanning and adjusting test results in accordance with aspects of the present invention.

FIG. 9 illustrates details of an embodiment of a process 900 for processing a test strip 265 such as is shown in FIG. 8. At stage 910, the test sample scan is initiated, with the sample being moved relative to the detector. As described previously herein, this may be done in any of several ways. As the test strip is moved across the detector 235, it may be illuminated by a source such as source 225 so that it emits or reflects a detectable output such as when a target analyte is present. At stage 915, one or more indicia and/or one or more test strips may be detected by the detector 235. Emissions or reflections from the test strip may be read in response to detection of an associated indicia as a reference location. Emissions or reflections from the indicia may be used to trigger reads of the test strip. The detection may be of radiation emitted or reflected from the test strip, and may represent one, two or three dimensional emission or reflection detection. The detected emissions or reflections may be incorporated into a detection signal that may then be sent to a processor, such as processor 240.

At stage 920, the positional alignment and/or motion of the test strip may be determined in one or more software modules. This may be done by, for example, comparing the relative timing of emissions or reflection data in the detection signal from the indicia and/or test strips and/or may be done in one, two or more dimensional processing depending the nature of the signal. Likewise, motion, velocity and/or variations of these, as well as other related information, may be determined at stage 925 based on the received emissions or reflections from the indicia(s) and/or test strip(s). Correlation of detection signals with indicia reference patterns may be used to implement this stage. A set of corrected detection data may be provided as an output of this stage.

At stage 930, the raw detected test strip data may be adjusted based on the alignment and/or motion determinations and/or corrected detection data made in stages 920 and 925 to generate test result output data. The data may, for example, be used to adjust the relative level of the received test strip emissions based on the motion of the test strip. In addition, the adjustment may be used to match test strip data at particular test lines to reference positioning determined based on the indicia. This may be used to map the test strip results to particular test samples to provide corresponding output(s). Data associated with motion detection may also be used to correct for variation in feed speeds of the sample through the scanner. In some implementations, motion and/or position data detected from the indicia may be used in a control or feedback loop to trigger or control emissions from the source so at to illuminate the sample at an appropriate time and/or for detection of sample emissions or reflections at an appropriate time, such as within predefined timing window(s).

At stage 935, the test result output data may be output and/or stored in a memory for further review and/or processing. Output test results may include quantitative data regarding presence or absence of a target or analyte in the sample. In some embodiments, the test result output data may be used to provide a test result output provided on a display or other output device. Alternately or in addition, the output may be stored on a memory device via a data port and/or may be provided via an I/O interface to an external device or system.

As noted previously, in typical, embodiments, the microprocessor 240 and software modules may also provide a quantitative determination for the assay as an output. For example, a positive or negative result for each test line 267 within the testing region 260 can be provided based on a read of the test sample and associated processing of the read in the microprocessor, such as is described previously herein. For example, detection of a target illumination from a test line 267 may be used as the basis for a quantitative positive result, and may be adjusted based on the indicia and/or motion or position determination. In addition, information regarding the concentration of analyte in the sample can be provided. The information may be correlated such that indicators of risk or presence of a disease or disorder are provided by the scanning device. The information may optionally be input into a decision support system and processed to provide an enhanced assessment of the risk of a medical condition. In addition, information from the test may be provided on a display of the device 215, either in a visual or audible fashion, or both.

The microprocessor 240 may also control specific operations of the scanning device 215 and control of the various functionalities of the device 215, including mechanical, optical and/or electronic functionality. The microprocessor 240 may be a central processor that controls the functionality through a bus structure or other communications interface. The microprocessor 240 may be implemented by distributing the processing functions amongst one or more of the various components of the scanning device. As noted previously, the microprocessor 240 may comprise one or more physical devices such as microprocessors, microcontrollers, DSP devices, ASICS, FPGAs or other programmable devices as are known or developed in the art. The microprocessor 240 may further incorporate memory to store data and/or instructions to perform the functions as described herein, as well as others.

The scanning device 215 may be provided with additional functional features including, for example, a user interface. 275, communication module 280, data port 285, memory 287, power supply 290, alignment system 257, and light shield 259 each to be described in more detail below. Any or all of these functionalities may be included in the scanning device 215 as is appropriate for the desired use.

The user interface 275 may be used for operating the device and viewing the results. The user interface 275 may include, for example, a keypad and/or display such as a small monochromatic or color LCD display. The user interface 275 may include technology that allows for the user to touch and select appropriate settings for use of the device such as a touch-screen display. Alternative interfaces may be provided as well, for example, a keyboard, mouse, track ball, or other user interface devices.

A data port 285 may be used with the scanning device 215. The data port 285 may be a ROM chip socket configured to receive a removable ROM chip or a SD type memory card slot configured to receive a memory card or the like. The data port 285 and associated storage devices can be used to store and/or backup data or lot-specific method parameters, update software, store program instructions, control and calibrate curves, operational data, history logs and other information that may be used with the device 215. The data port 285 and associated storage devices may be used for saving results in order to transfer the information to an information system such as a laboratory information system (LIS) or system personal computer (PC) or the like. The device may also include a communication module 280 that can transmit such information from the device to an LIS or PC. The communication module 280 may be wired or a wireless transmitter, a Bluetooth, bi-directional communications interface, infrared interface, RS-232 interface, RF interface, network interface or other communications interface. Information transmitted can include test results, statistics and other information as well as the receipt of information and instructions from external sources.

The memory 287 may be used to provide storage for program data or other data used by the microprocessor 240 during operation of the device 215. The memory 287 may be implemented using various RAM or ROM memory devices. The memory 287 may be used to store operating instructions and to provide memory registers for operating and storage. Memory 287 may also be used in conjunction with the data port 285 and associated storage devices. The memory 287 is generally used to store only data that is accessed frequently or rapidly.

The scanning device 215 may also include a power supply 290. The power supply 290 can include batteries, solar cells, transformers used to convert an AC. power source or other techniques to provide the appropriate power levels to the components of the device 215. In an embodiment, the power supply 290 can be rechargeable batteries such as, for example, NiCad or Nickel Metal Hydride batteries which can be recharged using a charger connected to AC power from a conventional wall outlet. The power supply 290 may be associated with a button 277 or other mechanism that a user can actuate in order to activate the power supply 290 and turn on the device 215.

As shown in FIGS. 3 and 2A-2D, in one embodiment the scanning device 215 may include an alignment system 257. The alignment system 257 can be used to assist in scanning a test device having corresponding alignment features 272 as shown in FIG. 5A. The alignment system 257 may be, for example, a pair of parallel rails positioned on either end of the aperture 255 near the interface region 250 of the device 215. The alignment system 257 can, for example, slideably interface with corresponding alignment features 272 present on the surface of the test device 220. The alignment features 272 of the test device 220 can be, for example, a pair of longitudinal channels. Alternatively, the alignment features 272 of the test device 220 can include raised tracks over which the alignment features 272 of the scanning device 215 can use as a guide during a swipe (see FIG. 2D). The configuration of the alignment system 257 and corresponding alignment features 272 can vary.

A light shield 259 may also be attached to the interface region 250 of the scanning device 215 (see FIG. 2B). The light shield 259 surrounds the interface region 250 and the aperture 255 of the device 215 on one or more sides. The light shield 259 as well as the alignment system 257 may block ambient light from entering the device 215 or the diagnostic lane 260 of the test device 220 during use. The alignment system 257 and light shield 259 can be integral with the chassis 245 or modular such that they couple to the distal portion of the device 215 near the interface region 250.

Example Work Flow and Methods

It should be appreciated that a sample collection device (SCD) may likewise be included in the diagnostic assay systems described herein. In general, a sample can be processed using a SCD which prepares a sample for application to a test device and reading a result via a scanner. For example, in some embodiments, a sample may be obtained or added to a SCD and one or more analytes contacted with reagents present in the SCD (e.g., detection and capture probes, and/or extraction reagents). The sample can then be processed and transferred through the SCD to the test device and read with a scanner.

For example, the sample mixture may enter the test device as is known in the art. The sample can be driven by capillary force and/or by wash buffer comprised in the test device so as to allow any analyte-probe complex to pass through the lateral flow membrane contained in the test device. Capture probes and complementary immobilized capture moieties bind or hybridize to each other in predetermined lines or spots on the lateral flow membrane, whereby detection probes (via conjugate labels contained thereon) will provide a detectable signal which can subsequently be read to determine which analytes were present in the sample processed.

Subsequently, the test device may be read with a scanning device to detect presence of a detectable signal at one or more defined lines and/or indicia on the test device. To read the test lines with bound analyte, the user holds the chassis of the scanning device and swipes it over the diagnostic lane of the test device with the interface region pointing towards the test strip. The test device can be read in a Single pass over the diagnostic lane or more than one pass over the test device. The test device and scanning device are freely movable relative to each other, meaning the scanning device can be freely moved by the user's hand with respect to the test device and vice versa. In certain embodiments, the test device is not inserted or loaded into the scanning device.

Information regarding the analyte of interest, indicators of risk, presence of a disease or disorder, patient information, test information may be provided upon swiping the scanning device over the test device. The information may optionally be input into a decision support system and processed to provide an enhanced assessment of the risk of a Medical condition. The scanning device can automatically display, print, save or upload the results. The scanning devices described herein are designed to have simple controls and a user interface such that assays are read and recorded without needing interpretation.

It should be appreciated that the scanner may be incorporated into a kit. In an embodiment, the kit may include one or more test devices and a hand-held scanner. In an embodiment, the kit further includes a sample collection device.

As certain changes may be made without departing from the scope of the present subject matter described herein, it is intended that all matter contained in the above description or shown in the accompanying drawings be interpreted as illustrative and not in a literal sense (and thus, not limiting).

Practitioners of the art will realize that the method, device and system configurations depicted and described herein are examples of multiple possible system configurations that fall within the scope of the current subject matter described herein.

While the subject matter described herein has been described with reference to the specific embodiments thereof, it should be understood by those skilled in the art that various changes may be made and equivalents may be substituted without departing from the true spirit and scope of the subject matter described herein. In addition, many modifications may be made to adapt a particular situation, material, composition of matter, process, process step or steps, to the objective and scope of the subject matter described herein. All such modifications are intended to be within the scope of the claims appended hereto.

Throughout this application, various publications, patents and published patent applications may be cited. The disclosures of these publications, patents and published patent applications referenced in this application are hereby incorporated by reference in their entirety into the present disclosure. Citation herein by the Applicant of a publication, published patent application, or patent is not an admission by the Applicant of said publication, published patent application, or patent as prior art. Accordingly, all publications and patents cited in this specification are herein incorporated by reference as if each individual publication or patent were specifically and individually indicated to be incorporated by reference.

While this specification contains many specifics, these should not be construed as limitations on the scope of an invention that is claimed or of what may be claimed, but rather as descriptions of features specific to particular embodiments. Certain features that are described in this specification in the context of separate embodiments may also be implemented in combination in a single embodiment. Conversely, various features that are described in the context of a single embodiment may also be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

In one or more exemplary embodiments, the functions, processes and methods described herein may be implemented in hardware, software, firmware, or any combination thereof. If implemented in software, the functions may be stored on or encoded as one or more instructions or code on a computer-readable medium. Computer-readable media includes computer storage media. Storage media may be any available media that may be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

It is understood that the specific order or hierarchy of steps or stages in the processes disclosed is an example of exemplary approaches. Based upon design preferences, it is understood that the specific order or hierarchy of steps in the processes may be rearranged while remaining within the scope of the present disclosure. Accompanying method claims may present elements of the various steps in a sample order, and are not meant to be limited to the specific order or hierarchy presented.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative; the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c.

It is intended that the following claims and their equivalents define the scope of the invention.

We claim:

1. A device, comprising:
an energy source configured to generate an excitation signal;
an optical assembly coupled to the energy source, the optical assembly configured to direct the excitation signal onto a test device, wherein the test device comprises one or more test lines and one or more indicia and wherein the optics assembly is configured to pass the energy source to the one or more test lines and the one or more indicia in order to energize the one or more test lines and the one or more indicia;
a detector configured to detect a response signal from the test device in response to the excitation signal, the response signal indicative of one or more indicia and one or more test lines; and
a microprocessor configured to generate test result data based on the response signal.

2. The device of claim 1, wherein the detector is a single detector configured to detect an emission or radiation from the one or more test lines and from the one or more indicia as the response signal.

3. The device of claim 1, further comprising a chassis coupled to one or more of the energy source, the optical assembly, the detector, or the microprocessor.

4. The device of claim 1, further comprising:
an aperture configured to permit the excitation signal to be directed onto the test device; and
a shield configured to surround the aperture to prevent entry of ambient light.

5. The device of claim 1, wherein the microprocessor is further configured to:
detect, based on the response signal, relative movement between the apparatus and the test device; and
when generating the test result data, compensate for the relative movement.

6. The device of claim 1, wherein the microprocessor is further configured to:
detect, based on the response signal, a relative angular offset between the apparatus and the test device; and
when generating the test result data, compensate for the relative angular offset.

7. The device of claim 1, wherein the detector includes one or more of a photomultiplier tube, photodiode, a PIN photodiode, a silicone photodiode, a differential photodiode, a double diode, a fourfold diode, a double wedge diode, a circular ring diode, one or more photo diode lines, a matrix photo diode, a PIN array, a linear diode array, a photo diode array (PDA), a charge-coupled device (CCD), a CMOS device or a light emitting diode (LED) photodiode.

8. The device of claim 1, wherein the detector is configured to detect one or more of reflectance, transmission, fluorescence, chemo-bioluminescence, magnetic, electromagnetic or an electric current.

9. A method, comprising:
   generating an excitation signal;
   directing the excitation signal onto a test device, wherein the test device comprises one or more test lines and one or more indicia, and wherein the excitation signal is directed towards the one or more test lines and the one or more indicia;
   detecting, in response to the excitation signal, a response signal from the test device, the response signal indicative of one or more indicia and one or more test lines; and
   generating test result data based on the response signal.

10. The method of claim 9, wherein the detector is a single detector configured to detect an emission or radiation from the one or more test lines and from the one or more indicia as the response signal.

11. The method of claim 9, further comprising detecting, based on the response signal, relative movement between the apparatus and the test device, the generating the test result data including compensating for the relative movement.

12. The method of claim 9, further comprising detecting, based on the response signal, a relative angular offset between the apparatus and the test device, the generating the test result data including compensating for the relative angular offset.

13. The method of claim 9, wherein the response signal is detected via one or more of a photomultiplier tube, photodiode, a PIN photodiode, a silicone photodiode, a differential photodiode, a double diode, a fourfold diode, a double wedge diode, a circular ring diode, one or more photo diode lines, a matrix photo diode, a PIN array, a linear diode array, a photo diode array (PDA), a charge-coupled device (CCD), a CMOS device or a light emitting diode (LED) photodiode.

14. The method of claim 9, the detecting including detecting one or more of reflectance, transmission, fluorescence, chemo-bioluminescence, magnetic, electromagnetic or an electric current.

15. The method of claim 9, the generating the test result data including employing one or more of data reduction, curve fitting, or a trained neural network.

16. A kit, comprising:
   a test device;
   a scanner device, comprising:
      an energy source configured to generate an excitation signal during use;
      an optical assembly coupled to the energy source, the optical assembly configured to direct the excitation signal onto the test device, wherein the test device comprises one or more test lines and one or more indicia, and wherein the optics assembly is configured to pass the energy source to the one or more test lines and the one or more indicia in order to energize the one or more test lines and the one or more indicia;
      a detector configured to detect a response signal from the test device in response to the excitation signal, the response signal indicative of one or more indicia and one or more test lines; and
      a microprocessor configured to generate test result data based on the response signal.

17. The kit of claim 16, wherein the test device includes a test strip, the test strip including the one or more test lines, the test device including the one or more indicia.

18. The kit of claim 16, further including a sample collection device.

19. The kit of claim 16, wherein the microprocessor is further configured to:
   detect, based on the response signal, relative movement between the apparatus and the test device during use; and
   when generating the test result data, compensate for the relative movement.

20. The kit of claim 16, wherein the microprocessor is further configured to:
   detect, based on the response signal, a relative angular offset between the apparatus and the test device during use; and
   when generating the test result data, compensate for the relative angular offset.

\* \* \* \* \*